US008952197B2

(12) United States Patent
DeMattei et al.

(10) Patent No.: US 8,952,197 B2
(45) Date of Patent: Feb. 10, 2015

(54) PROCESSES FOR THE PREPARATION OF 5-HT$_{2C}$ RECEPTOR AGONISTS

(75) Inventors: John A. DeMattei, Berthoud, CO (US); Carlos Marlon, Chula Vista, CA (US); Ryan O. Castro, San Diego, CA (US); Tsung-Hsun Chuang, San Diego, CA (US); Mark Allen Hadd, San Diego, CA (US); Xiao-Xiong Lu, San Diego, CA (US); Mark Macias, San Diego, CA (US); Stephen M. Shaw, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 3 days.

(21) Appl. No.: 13/378,797

(22) PCT Filed: Jun. 17, 2010

(86) PCT No.: PCT/US2010/039004
§ 371 (c)(1),
(2), (4) Date: Feb. 15, 2012

(87) PCT Pub. No.: WO2010/148207
PCT Pub. Date: Dec. 23, 2010

(65) Prior Publication Data
US 2012/0142967 A1    Jun. 7, 2012

Related U.S. Application Data

(60) Provisional application No. 61/268,930, filed on Jun. 18, 2009.

(51) Int. Cl.
C07C 209/00  (2006.01)
C07C 213/08  (2006.01)
C07C 17/16   (2006.01)
C07C 209/08  (2006.01)
C07C 209/74  (2006.01)
C07C 211/29  (2006.01)

(52) U.S. Cl.
CPC .............. *C07C 213/08* (2013.01); *C07C 17/16* (2013.01); *C07C 209/08* (2013.01); *C07C 209/74* (2013.01); *C07C 211/29* (2013.01)
USPC ....................................... 564/376

(58) Field of Classification Search
None
See application file for complete search history.

(56) References Cited

U.S. PATENT DOCUMENTS

| | | |
|---|---|---|
| 2,900,415 A | 8/1959 | Biel |
| 3,652,543 A | 3/1972 | Hoegerle |
| 3,716,639 A | 2/1973 | Hoegerle et al. |
| 3,795,683 A | 3/1974 | Brossi et al. |
| 4,108,989 A | 8/1978 | Holden |
| 4,111,957 A | 9/1978 | Holden et al. |
| 4,210,729 A | 7/1980 | Hermans et al. |
| 4,210,749 A | 7/1980 | Shetty |
| 4,233,217 A | 11/1980 | Shetty |
| 4,541,954 A | 9/1985 | Borowski et al. |
| 4,584,293 A | 4/1986 | Reiffen et al. |
| 4,737,495 A | 4/1988 | Bomhard et al. |
| 4,762,845 A | 8/1988 | Chu et al. |
| 4,957,914 A | 9/1990 | Clark et al. |
| 4,988,690 A | 1/1991 | Effland et al. |
| 5,015,639 A | 5/1991 | Berger et al. |
| 5,178,786 A | 1/1993 | Jahnke et al. |
| 5,247,080 A | 9/1993 | Berger et al. |
| 5,275,915 A | 1/1994 | Kojima et al. |
| 5,387,685 A | 2/1995 | Powell et al. |
| 5,412,119 A | 5/1995 | Brussee et al. |
| 5,422,355 A | 6/1995 | White et al. |
| 5,691,362 A | 11/1997 | McCormick et al. |
| 5,750,520 A | 5/1998 | Danilewicz et al. |
| 5,795,895 A | 8/1998 | Anchors |
| 5,856,503 A | 1/1999 | Aebi et al. |
| 5,861,393 A | 1/1999 | Danilewicz et al. |
| 5,925,651 A | 7/1999 | Hutchinson |
| 5,939,415 A | 8/1999 | Laufer et al. |
| 5,942,535 A | 8/1999 | Laufer et al. |
| 5,958,943 A | 9/1999 | Laufer et al. |
| 6,087,346 A | 7/2000 | Glennon et al. |
| 6,218,385 B1 | 4/2001 | Adam et al. |
| 6,342,501 B1 * | 1/2002 | Townsend et al. ......... 514/265.1 |
| 6,900,313 B2 | 5/2005 | Wasserscheid et al. |
| 6,953,787 B2 | 10/2005 | Smith et al. |
| 6,972,295 B2 | 12/2005 | Hagmann et al. |
| 7,514,422 B2 | 4/2009 | Smith et al. |
| 7,704,993 B2 | 4/2010 | Smith et al. |

(Continued)

FOREIGN PATENT DOCUMENTS

AU    515236 B2    3/1981
CA    1090797      12/1980

(Continued)

OTHER PUBLICATIONS

Vogel's Textbook of Practical Organic Chemistry 5$^{th}$ edition, 1989, 4 pages. (front matter, and 558-559).*
Barbière, "Estérification nitrique et nitration d'amino-alcools," Bulletin de la Société Chimique de France, (1944), 5(11):470-480.
Ichii, "Friedel-crafts aralkylation. II. The AlCl3 Ch2NO2-catalyzed phenethylation of benzene and toluend with 2-arylethyl chlorides in a nitromethane solution," Bulletin of the Chemical Society of Japan, (1972), 45(9):2810-2813.
International Preliminary Report on Patentability for PCT/US2010/039004, dated Oct. 14, 2011.
International Search Report for PCT/US2010/039004, dated Jun. 9, 2011.
U.S. Appl. No. 13/309,497, filed Dec. 1, 2011, Wolgast et al.
U.S. Appl. No. 13/425,669, filed Mar. 21, 2012, Agarwal et al.

(Continued)

*Primary Examiner* — Clinton Brooks

(57) ABSTRACT

The present invention relates to processes and intermediates useful in the preparation of (R)-8-chloro-1-methyl-2,3,4,5-tetrahydro-1H-3-benzazepine (lorcaserin), a serotonin (5-HT) receptor modulator that is useful in the treatment of for example, central nervous system disorders, such as obesity.

44 Claims, 2 Drawing Sheets

(56) References Cited

U.S. PATENT DOCUMENTS

| | | | |
|---|---|---|---|
| 7,977,329 | B2 | 7/2011 | Smith et al. |
| 8,153,621 | B2 | 4/2012 | Behan et al. |
| 8,168,624 | B2 | 5/2012 | Agarwal et al. |
| 8,168,782 | B2 | 5/2012 | Weigl et al. |
| 2004/0101575 | A1 | 5/2004 | Hinz |
| 2007/0060568 | A1 | 3/2007 | Smith et al. |
| 2007/0275949 | A1 | 11/2007 | Smith et al. |
| 2008/0045502 | A1 | 2/2008 | Wolgast et al. |
| 2009/0143576 | A1 | 6/2009 | Weigl et al. |
| 2009/0264598 | A1* | 10/2009 | Bittner et al. ............... 525/231 |
| 2010/0004223 | A1 | 1/2010 | Agarwal et al. |
| 2010/0173894 | A1 | 7/2010 | Brian et al. |
| 2010/0305316 | A1 | 12/2010 | Gharbaoui et al. |
| 2011/0015438 | A1 | 1/2011 | Carlos et al. |

FOREIGN PATENT DOCUMENTS

| | | | |
|---|---|---|---|
| CA | 2197789 | | 8/1995 |
| CA | 2325741 | A1 | 10/1999 |
| CH | 500194 | | 1/1971 |
| CN | 102126988 | | 7/2011 |
| DE | 1944121 | | 3/1970 |
| DE | 1914456 | | 6/1971 |
| DE | 3418270 | | 11/1985 |
| EP | 0007070 | | 1/1980 |
| EP | 0080779 | A1 | 6/1983 |
| EP | 00027695 | B1 | 10/1983 |
| EP | 0096838 | | 12/1983 |
| EP | 0161350 | A1 | 11/1985 |
| EP | 0174118 | | 3/1986 |
| EP | 0204349 | | 12/1986 |
| EP | 245997 | A2 | 11/1987 |
| EP | 0285287 | A2 | 10/1988 |
| EP | 0285919 | B1 | 10/1988 |
| EP | 0285287 | A3 | 8/1990 |
| EP | 0987235 | A1 | 3/2000 |
| EP | 1074549 | A2 | 2/2001 |
| EP | 0987235 | B1 | 3/2003 |
| EP | 1074549 | B1 | 11/2003 |
| EP | 1411881 | B1 | 4/2005 |
| EP | 1838677 | B1 | 9/2009 |
| FR | 2518544 | A1 | 6/1983 |
| GB | 1196229 | | 6/1970 |
| GB | 1221324 | | 2/1971 |
| GB | 1225053 | | 3/1971 |
| GB | 1247306 | | 9/1971 |
| GB | 1268243 | | 3/1972 |
| GB | 1542317 | | 3/1979 |
| GB | 1599705 | | 10/1981 |
| GB | 2133401 | | 7/1984 |
| ID | 3315106 | A1 | 11/1983 |
| JP | 62-267250 | | 11/1987 |
| JP | 502723 | | 8/1990 |
| JP | 5339263 | | 12/1993 |
| JP | 06298746 | | 10/1994 |
| JP | 08134048 | | 5/1996 |
| JP | 09030960 | | 2/1997 |
| JP | 90987258 | | 3/1997 |
| JP | 2000 44533 | | 2/2000 |
| JP | 2001 89472 | | 4/2001 |
| NL | 7807819 | | 7/1978 |
| SU | 1238732 | A3 | 6/1986 |
| WO | WO 88/07526 | A1 | 10/1988 |
| WO | WO 88/07858 | | 10/1988 |
| WO | WO 91/19698 | | 12/1991 |
| WO | WO 93/00094 | | 1/1993 |
| WO | WO 9316997 | | 9/1993 |
| WO | WO 95/13274 | | 5/1995 |
| WO | WO 96/04271 | | 2/1996 |
| WO | WO 96/05194 | A1 | 2/1996 |
| WO | WO 96/33993 | A1 | 10/1996 |
| WO | WO 97/24364 | A1 | 7/1997 |
| WO | WO 98/06701 | A1 | 2/1998 |
| WO | WO 98/40385 | A1 | 9/1998 |
| WO | WO 99/24411 | A1 | 5/1999 |
| WO | WO 02/40471 | A2 | 5/2002 |
| WO | WO 02/48124 | A2 | 6/2002 |
| WO | WO 02/074746 | | 9/2002 |
| WO | WO 03/000663 | A1 | 1/2003 |
| WO | WO 03/027068 | A2 | 4/2003 |
| WO | WO 03/057161 | | 7/2003 |
| WO | WO 03/062392 | A2 | 7/2003 |
| WO | WO 03/086306 | A2 | 10/2003 |
| WO | WO 2004/037788 | | 5/2004 |
| WO | WO 2005/003096 | A1 | 1/2005 |
| WO | WO 2005/019179 | A2 | 3/2005 |
| WO | WO 2005/042490 | A1 | 5/2005 |
| WO | WO 2005/042491 | A1 | 5/2005 |
| WO | WO 2006/006933 | A2 | 1/2006 |
| WO | WO 2006/013209 | A2 | 2/2006 |
| WO | WO 2006/043710 | | 4/2006 |
| WO | WO 2006/069363 | A2 | 6/2006 |
| WO | WO 2006/071740 | A2 | 7/2006 |
| WO | WO 2007/120517 | A2 | 10/2007 |
| WO | WO 2008/070111 | A2 | 6/2008 |
| WO | WO 2009/111004 | A1 | 9/2009 |
| WO | WO 2010/148207 | | 12/2010 |

OTHER PUBLICATIONS

U.S. Appl. No. 60/372,058, filed Apr. 12, 2002, Smith et al.
U.S. Appl. No. 60/405,495, filed Aug. 23, 2002, Smith et al.
U.S. Appl. No. 60/434,607, filed Dec. 18, 2002, Smith et al.
U.S. Appl. No. 60/479,280, filed Jun. 17, 2003, Wolgast et al.
U.S. Appl. No. 60/512,967, filed Oct. 21, 2003, Burbaum et al.
U.S. Appl. No. 60/638,221, filed Dec. 21, 2004, Agarwal et al.
U.S. Appl. No. 60/789,191, filed Apr. 3, 2006, Xiong et al.
U.S. Appl. No. 60/873,036, filed Dec. 5, 2006, Gharbaoui et al.
U.S. Appl. No. 61/068,102, filed Mar. 4, 2008, Carlos, et al.
Baindur, et al., "(±)-3-Allyl-7-halo-8-hydroxy-1-phenyl-2,3,4,5-tetrahydro-1H-3-Benzazepines as Selective High Affinity Di Dopamine Receptor Antagonists: Synthesis and Structure-Activity Relationship", J. Med. Chem., 35:67-72 (1992).
Barbiere, Estérification nitrique et nitration d'amino-alcools. Mémoires Présentés a La Société chimique (Feb. 2, 1944). French language.
Barnes, Pharmacological Strategies for Relapse Prevention in Schizophrenia, Psychiatry, 3(10):37-40 (2004).
Bickerdike, "5-HT2C Receptor Agonists as Potential Drugs for the Treatment of Obesity," Current Topics in Medicinal Chemistry, vol. 3:pp. 885-897 (2003).
Biel, et al. Bronchodilators, N-Substituted Derivatives of 1-(3',4'-Dihydroxyphenyl)-2-aminoethanol (Artenerol), J. Am. Chem. Soc. 1954, vol. 76, pp. 3149-3153.
Bosch, et al., "Studies on the Synthesis of Pentacyclic Strychnos Indole Alkaloids. Photocyclization of N-Chloroacetyl-1,2,3,4,5,6-hexahydro-1,5-methanoazocino [4,3-b] Indole Derivatives", Tetrahedron, 41(12):2557-66 (1985).
Bremner, "Seven Membered Rings," Institute for Biomolecular Science Dept. of Chemistry, University of Wollongong; "Progress in Heterocyclic Chemistry 13", Pergamon Press, Ch. 7:340-77 (2001).
Casy, et al., "Some Arylalkylamino Analogs of Acyclic Analgetics", J Med Chem, (1968), 11(3):599-601.
Chahal et al., IDdb Meeting Report 2000, May 17-18.
Chang, et al., "Dopamine Receptor Binding Properties of Some 2,3,4,5-Tetrahydro-1H-3-Benzazepine-7-ols With Non-Aromatic Substituents in the 5-Position", Bioorganic & Med. Chem. Letters, (1992) 2(5);399-402.
Chumpradit, et al., "(±)-7-Chloro-8-hydroxyl-1-(4'-[125 I]iodophenyl)-3-methyl-2,3,4,5-tetrahydro-1H-3-benzazepine: A Potential CNS D-1 Dopamine Receptor Imaging Agent", J. Med. Chem., 32:1431-5 (1989).
Clark, et al., "1,9-Alkano-Bridged 2,3,4,5-Tetrahydro-1H-3-benzazepines With Affinity for the A2-Adrenoceptor and the 5-HT1A Receptor", J. Med. Chem., 33:633-41 (1990).
Deady et al. "Synthesis of some tetrahydro-2-a and 3-benzazepines, and of hexahydro-3-benzazocine." JCS Perkin I, 782-3 (1973).
Demarinis et al., "Development of an Affinity Ligand for Purification of A2-Adrenoceptors From Human Platelet Membranes", J. Med. Chem., 27, 918-921 (1984).

(56) References Cited

OTHER PUBLICATIONS

Di Chiara et al. "Nucleus accumbens shell and core dopamine: differential role in behavior and addiction." (2002) Behavioural Brain Research, 137: 75-114.

Di Chiara et al., "Reward System and Addiction: What Dopamine Does and Doesn't Do", Current Opinion in Pharmacology 7:69-76 (2007).

Di Giovanni et al., "Serotonin/dopamine interaction—Focus on 5-HT2c receptor, a new target of psychotropic drugs," Indian Journal of Experimental Biology, vol. 40:1344-1352 (2002).

Di Matteo et al., "Role of 5-HT2c Receptors in the Control of Central Dopamine Function," Trends in Pharmacological Sciences, 22(5):229-232 (2001).

Diagnostic and Statistical Manual of Mental Disorders, 4th edition, Text Revision,Washington, DC, American Psychiatric Association, 2000.

Dixit et al., "Genes Acting on Central Nervous System: Part XXIII: 2-Substituted 1,2,3,4,6,7,12, 12a-octahydropyrazino[2,i-b][3] benzazepines & 3-Substituted 1,2,3,4, 4a, 5, 6,11-Octahydropyrazin[i,2-b][2] benzazepines", CDRI Communication No. 1969,893-97 (1974).

Draper, et al., "Novel Stereoselective Syntheses of the Fused Benzazepine Dopamine D1 Antagonist (6aS,13bR)-11-Chloro-6,6a,7,8,9,13b-hexahydro-7-methyl- 5H-benzo[d]naphth[2,1-b]azepin-12-ol (Sch 39166): 2. I-Homophenylalanine-Based Syntheses", Organic Process Research & Development, 2(3)186-93 (1998).

Draper, et al., "Novel Stereoselective Syntheses of the Fused Benzazepine DopamineD1 Antagonist (6aS,13bR)-11-Chloro-6,6a,7,8,9,13b-hexahydro-7-methyl-5H- benzo[d]naphth[2,1-b]azepin-12-ol (Sch 39166): 1. Aziridinium Salt Based Syntheses", Organic Process Research & Development, 2(3):175-85 (1998).

Flannery-Schroeder, "Reducing Anxiety to Prevent Depression," Am. J. Prev. Med. 31(6S1):S 136-S 142 (2006).

Fuchs et al. "Total synthesis of (±)-lennoxamine and (±)-aphanorphine by intramolecular electrophilic aromatic substitution reactions of 2-amidoacroleins." Organic Lett. 3(34):3923-5 (2001).

Gallant et al., "U-22,394A: a controlled evaluation in chronic schizophrenic patients," Current Therapy Research, 9(11):579-81(1967).

Gardent et al. "Sur quelques proprietes de l'amino-2-bromo-4 1H benzazepine-3 et de ses derives." Bulletin de la Societe Chimique de France, 2:600-5 (1968).

Gerace et al., "Predictors of Weight Increases over 7 Years in Fire Fighters and Paramedics," Preventive Medicine, 25:593-600 (1996).

Gerritz et al., "Two General Routes to 1,4-disubstituted-2,3,4,5-tetrahydro-1H-3-benzazepines," Organic Letters, 2(25):4099-102 (2000).

Gobert et al., "Serotonin2c Receptors Tonically Suppress the Activity of Mesocortical Dopaminergic and Adrenergic, but Not Serotonergic, Pathways: A Combined Dialysis and Electrophysical Analysis in the Rat," Synapse, 36:205-221 (2000).

Gombar, et al., "Pharmacokinetics of a Series of 6-Chloro-2,3,4,5-tetrahydro-3-substituted-1H-3-benzazepines in Rats", Drug Metabolism and Disposition, 16(3):367-72 (1988).

Green & Wuts et al. "Protective Groups in Organic Synthesis." 3rd Ed. Wiley & Sons (1999) (cited reference is excessively voluminous; kindly request delivery if desired).

Greisser, "Polymorphism in the pharmaceutical industry." Ed. Rolf Hilfiker, Wiley-VCH Verlag GmbH & Co. 211-233 (2006).

Guillory, "Polymorphism in Pharmaceutical Solids," ed. Harry G. Brittain, Marcel Dekker, Inc., vol. 95: pp. 202-209 (1999).

Halford et al., "Serotonergic Drugs: Effects on Appetite Expression and Use for the Treatment of Obesity," Drugs 67(1):27-55 (2007).

Halford, et al., "o-Phenylenediacetimide and Other Compounds Related to 3,1H-benzazepine," J. Org. Chem. 17:1646-52 (1952).

Halford, J.C.G., "Obesity Drugs in Clinical Development," Current Opinion in Investigational Drugs 7(4):312-318 (2006).

Hasan et al., "Syntheses of N-Chloroacyl-β-phenylethylamine Derivatives", Indian J. Chem., 9:1022-4 (1971).

Hashima. Synthesis and biological activities of the marine bryozoan alkaloids convolutamines A,C and F, and lutamides A and C. Bioorganic & Medicinal Chem. 2000, vol. 8, No. 7, pp. 1757-1766.

Hassine-Coniac, et al., "Preparation et propriétés d'aldéhydes dans la série de la benzazépine-3," Bulletin de La Société Chimique de France, 11:3985-92 (1971) French Lang Only.

Haynes et al., "Occurrence of pharmaceutically acceptable anions and cations in the Cambridge Structural Database," J. Pharm. Sci. 94:10, pp. 2111-2120 (Oct. 2005).

Hazebroucq "Acces a des I-H, tetrahydro-2, 3, 4, 5 benzazepines-3 one-1 et a des hexahydro imidazo isoquinoleines," Ann. Chim. (1966) pp. 221-254.

Helferich et al. "Uber Derivate Einger chinolincarbonsauren," J. Fur Praktische Chemie, vol. 33, 1966, 39-48.

Hester et al., "Azepinoindoles. I. Hexahyclroazepino[4,5-b)indoles," J. Med. Chem, 11(1):101-106 (1968).

Heys et al., "A New Entry into C7-Oxygenated Tetrahydro-1H-3-benzazepines:Efficient Labeling with Carbon-14 in the Benzo Ring," J. Org. Chem., 54(19):4702-6 (1989).

Higgins et al., "Serotonin and drug reward: focus on 5-HT2c receptors," European Journal of Pharmacology, 480:151-162, (2003).

Hitzig, P., "Combined Serotonin and Dopamine Indirect Agonists Correct Alcohol Craving and Alcohol-Associated Neuroses," Journal of Substance Abuse Treatment, 11(5):489-90 (1994).

Ichii, Friedel-crafts Aralkylation. II.[1)] The $AlCl_3 \cdot CH_2NO_2$-catalyzed phenethylation of benzene and toluene with 2-arylethyl chlorides in a nitromethane solution. Bulletin Chem. Society Japan, vol. 45:2810-1813 (1972).

Im et al., "Positive Allosteric Modulator of the Human 5-HT2C Receptor," Molecular Pharmacology, 64: 78-84 (2003).

Jandacek, R.J., "APD-356 (Arena)," Current Opinion in Investigational Drugs (6(10):1051-1056 (2005).

Jenck et al., "Antiaversive effects of 5-HT2c receptor agonists and fluoxetine in a model of panic-like anxiety in rats," European Neuropsychopharmacology, 8:161(1998).

Jensen et al., "Potential Role of New Therapies in Modifying Cardiovascular Risk in Overweight Patients with Metabolic Risk Factors", Obesity 14 (Suppl. 3):143S-149S (2006).

Kaiser, et al., "6-(Phenylthio)-Substituted 2,3,4,5-Tetrahydro-1H-3-benzazepines, a Novel Class of Dopamine Receptor Antagonists and Neuroleptics", J. Med. Chem., 23(9):975-6 (1980).

Karasu et al., (2000) Practice Guideline for the Treatment of Patients with Major Depressive Disorder.

Klohr et al., "An Intramolecular Photocyclization to Form the Azepino[3,4,5-cd]Indole System," Synthetic Communications 18(7):671-4 (1988).

Koplan et al., "Preventing Childhood Obesity: Health in the Balance, Executive Summary", http://www.nap.edu/catalog/11015.html, 41 pages (2005).

Krull, et al. Synthesis and structure/NMDA receptor affinity relationships of 1-substituted tetrahydro-3-benzazepines. Bioorganic & Medicinal Chem. 12(6), 1439-1451. 2004.

Kuenburg et al., "Development of a Pilot Scale Process for the Anti-Alzheimer Drug (−)-Galantahmine Using Large-Scale Phenolic Oxidative Coupling and Crystallisation-Induced Chiral Conversion," Organic Process Research & Development, 3(6):425-31 (1999).

Lacivita et al., "Selective Agents for Serotonin2C (5-HT2C) Receptor," Current Topics in Medicinal Chemistry, vol. 6:pp. 1927-1970 (2006).

Ladd, et al., "Synthesis and Dopaminergic Binding of 2-Aryldopamine Analogues: Phenethylamines, 3-Benzazepines, and 9-(Aminomethyl)flourenes", J. Med. Chem., (1986) 29(10):1904-1912.

Lam et al. Canadian Consensus Guidelines for the treatment of seasonal affective disorder. Clinical & Academic Pub. Vancouver, BC Canada 2000.

Lennon et al., "Azabenzocycloheptenones. Part XVIII. Amines and amino-ketones of the tetrahydro-3-benzazepine-1-one series," J. Chem. Soc. Perkin Transacts. (1975) 7:622-626.

(56) References Cited

OTHER PUBLICATIONS

Lin et al., "Benzindene Prostaglandins. Synthesis of Optically Pure 15-Deoxy-U-68,215 and its Enantiomer via a Modified Intramolecular Wadsworth-Emmons-Witting Reaction," J. Org. Chem., 52(25):5594-601(1987).

MacDonald, et al., "Design and Synthesis of trans-3-(2-(4((3-(3-(5-methyl-1,2,4-oxadiazolyl))-phenyl)carboxamido)cyclohexyl)ethyl)-7-methylsulfonyl-2,3,4,5-tetrahydro-1H-3-benzazepine (SB-414796): A Potent and Selective Dopamine D3 Receptor Antagonist", J. Med. Chem., 46(23):4952-64 (2003).

Mondeshka (1990) Arch. Pharm. 323:829.

Moline et al., "Postpartum Depression: A Guide for Patients and Families," Expert Consensus Guidelines Series—Treatment of Depression in Woman 2001, Mar.: 112-113 (2001).

Muller et al., "Intracellular 5-HT2c-receptor dephosphorylation: a new target for treating drug addiction," Trends in Pharmacological Sciences, 27(9):455-58(2006).

Nagase et al., "An anhydrous polymorphic form of trehalose," Carbohydrate Research 337(2),167-173 (2002).

Nagle, et al. "Efficient Synthesis of β-Amino bromides", Tetrahedron Letters, 41 :30 11-4 (2000).

Nair et al., "Preparation of 2,3,4,5-tetrahydro-3,1H-benzazepine-2-one," Indian J. Chem., 5:169-70 (1967).

Navarro-Vazquez et al., "A study of aryl radical cyclization in enaminone esters", J. Org. Chem. 67:3213-20 (2002).

Neumeyer, et al., "Development of a High Affinity and Stereoselective Photoaffinity Label for the D-1 Dopamine Receptor: Synthesis and Resolution of 7-[125I]Iodo-8-hydroxy-3-methyl-1-(4'-azidophenyl)-2,3,4,5-tetrahydro-1H-3-benzazepine", J. Med. Chem., 33(2):521-6 (1990).

Nida Research Monograph 27,1979; Problems of Drug Dependence, 1979; AA Proceedings of the 41st Annual Scientific Meeting, The Committee on Problems of Drug Dependence, Inc.

Niendam et al., "Neurocognitive Performance and Functional Disability in the Psychosis Prodrome," Schizophrenia Research, 84:100-111 (2006).

Ohnmacht, et al. Naphtho[2,1-b][1,5]- and [1,2-f][1,4]oxazocines as Selective NK1 Antagonists Bioorganic & Medicinal Chem. 2004, vol. 12, No. 10, pp. 2653-266.

Okuno, et al., "Photocyclization of N-Chloroacetyl-2,5-Dimethoxyphenethylamine Synthesis of Pyrroloindoles", Chem. Pharm. Bull., 23(11):2584-90 (1975).

Orito et al., "Benzolactams-I: Alkylation of 1,2,4,5-tetrahydro-3-methyl-3H-3-benzazepin-2-one with sodium hydride and alkyl halide," Tetrahedron 36:1017-1021(1980) Pergamon Press Ltd.

Orito, et al., "Total Synthesis of Pseudo Type of Protopine Alkaloids", Heterocycles, 14(1):11-4 (1980).

Orito, et al., "Synthetic studies of Heterocyclic Compounds I, Alkylation and Acylation of 1,2,4,5-tetrahydro-3-methyl-3H-3-benzazepine-2-one." Bulletin of the Faculty of Engr. Hokkaido Univ. No. 96 (1979).

Paulekuhn et al., "Trends in active pharmaceutical ingredient salt selection based on analysis of the Orange Book Database." J. Med. Chem. 50:26, pp. 6665,6672 (2007).

Pauvert, et al., "Silver Nitrate-Promoted Ring Enlargement of 1-Tribromomethyl-1,2-Dihydro-and 1-Tribromethyl-1,2, 3,4-Tetrahydro-Isoquinoline Derivatives: Application to the Synthesis of the Anti-Anginal Zatebradine", Tetrahedron Letters, 44:4203-6 (2003).

Pawan et al., "Preliminary study on the effects of fenfluramine derivative, 'S992' in man," British Journal of Pharmacology, 41(2): 416P-417P (1971) (CAPLUS abstract).

Pecherer et al., "The Synthesis of Some 7- and 7,8-substituted 2,3,4,5-tetrahydro-1H-3-benzazepines," J. Heterocyclic Chemistry 8(5):779-783 (1971).

Pecherer, et al., "A Novel Synthesis of Aromatic Methoxy and Methylenedioxy Substituted 2,3,4,5-Tetrahydro-1H-3-benzazepines", J. Het. Chem., 9:609-16 (1972).

Perry, et al., Prospective Study of Risk Factors for Development of Non-Insulin Dependent Diabetes in Middle Aged British Men, BMJ, 310:560-4 (1995).

Pfeiffer, et al., "Dopaminergic Activity of Substituted 6-Chloro-1-phenyl-2,3,4,5-tetrahydro-1H-3-benzazepines", J. Med. Chem., 25(4):352-8 (1982).

Piesla et al., (2001) Schizophrenia Research 49: 95.

Porras et al., "5-HT$_{2A}$ and 5-HT$_{2C/2B}$ Receptor Subtypes Modulate Dopamine Release Induced in Vivo by Amphetamine and Morphine in Both the Rat Nucleus Accumbens and Striatum," Neuropsychopharmacology 26: 311-324 (2002).

Prous Science Integrity entry 156186, 2007.

Prous Science Integrity entry 354056, 2007.

Remington's Pharmaceutical Sciences, 17th ed., Mack Publishing Company, Easton Pa.: 1418 (1985).

Rothman R.B., "Treatment of Alcohol and Cocaine Addiction by the Combination of Pemoline and Fenfluramine: A Preliminary Case Series," Journal of Substance Abuse Treatment, 12(6):449-53 (1995).

Schaffner et al., "Preventing Severe Mental Illnesses—New Prospects and Ethical Challenges," Schizophrenia Research, 51:3-15 (2001).

Schlademan et al., "Synthesis of oxo- and 1-hydroxy-azobenzocycloalkanes," J. Chem. Soc. Perkin Transacts. (1972) 2:213-215.

Smith et al., "Discovery and SAR of New Benzazepines as Potent and Selective 5HT2c Receptor Agonists for the Treatment of Obesity," Bioorganic & Medicinal Chemistry Letters, 15(5):1467-1470 (2005).

Smith, B. M. et al., "Discovery and Structure—Activity Relationship of (1R)-8-Chloro-2,3,4,5-tetrahydro-1-methyl-1H-3-benzazepine (Lorcaserin), a Selective Serotonin 5-HT2c Receptor Agonist for the Treatment of Obesity," J. Med. Chem. 2008, 51, 305-313.

Tietze et al., "Efficient synthesis of 2, 3, 4, 5-tetrahydro-1H-3-benzazepines by intramolecular Heck reaction," Synthesis 876:880 (Sep. 1993).

Tsuang et al., Towards the Prevention of Schizophrenia, B245 Biol. Psychiatry, 48:349-356 (2000).

Van Oekelen et al., "5-HT2A and 5-HT2C receptors and their atypical regulation properties," Life Sciences, vol. 72:2429-2449 (2003).

Vanderlaan et al., "Synthesis and Oxidative Coupling of (±)-3-oxoreticuline," J. Org. Chem., 50(6):743-7 (1985).

Vink et al., "Risk Factors for Anxiety and Depression in the Elderly: A Review," J. Affect. Disord., vol. 106, p. 29-44, 2008.

Weinstock et al., "Separation of Potent Central and Renal Dopamine Agonist Activity in Substituted 6-chloro-2,3,4,5-tetrahydro-7,8-dihydroxy-1-phenyl-1H-3-benzazepines," J. Med. Chem., 23(9):973-5 (1980).

Wilk (1988) Pol. J. Chem. 62:895.

Williams, Chemistry Demystified 123 (2003).

Wise, R.A., "Addiction becomes a brain disease", (2000) Neuron, 26: 27-33.

Wisner et al., "Clinical practice. Postpartum depression." (2002) N. Engl. J. Med., 347(3): 194-199.

Woods et al., "Annual Report: Evaluation of New Compounds for Opioid Activity," National Institute on Drug Abuse, Proceedings of the 41st Annual Scientific Meeting (1979) pp. 356-401.

Wu et al., "Amino Diol Based Asymmetric Syntheses of a Fused Benzazepine as a Selective D1 Dopamine Receptor," Organic Process Research & Development, 1(5):359-64 (1997).

Yasuda et al., "A Novel and Stereoselective Synthesis of (±)-cephalotaxine and its Analogue," Tetrahedron Letters, 27(18):2023-6 (1986).

Yonemitsu, et al., "Photocyclization of Pharmacodynamic Amines. IV. Novel Heterocycles From N-Chloroacetyl-3,4-Dimethoxyphenethylamine", Journal of the American Chemical Society, 92(19):5686-90 (1970).

(56) References Cited

OTHER PUBLICATIONS

Yonemitsu, et al., "Photocyclization of Pharmodynamic Amines. II. X-Ray Analysis of Noncentrosymmetric Tetracyclic Indole", Journal of the American Chemical Society, 90(23):6522-3 (1968).

Yonemitsu, et al., "Photocyclizations of Tyrosines, Tyramines, Catecholamines, and Normescaline", Journal of the American Chemical Society, 90(3):776-84 (1968).

Yonemitsu, et al., "Photolysis of N-Chloroacetyl-O-Methyl-L-Tyrosine to an Azaazulene", Journal of the American Chemical Society, 89(4):1039-40 (1967).

Yoshinaga, et al., "Prevention of Mildly Overweight Children from Development of More Overweight Condition," Prevention Medicine, 38:172-174 (2004).

Zhang, et al. "Convolutamines A-E, Novel B-Phenylethylamine Alkaloids From Marine Bryozoan Amathia Convolute", Chem. Lett. 1994, vol. 12, pp. 2271-4.

\* cited by examiner

PROCESSES FOR THE PREPARATION OF 5-HT$_{2C}$ RECEPTOR AGONISTS

This application is a National Stage Application of PCT/US2010/039004 filed Jun. 17, 2010, which claims priority from U.S. Provisional Application No. 61/268,930, filed Jun. 18, 2009, each of which is incorporated herein by reference in its entirety.

FIELD OF THE INVENTION

The present invention relates to processes and intermediates useful in the preparation of (R)-8-chloro-1-methyl-2,3,4,5-tetrahydro-1H-3-benzazepine (lorcaserin), a serotonin (5-HT) receptor modulator that is useful in the treatment of, for example, central nervous system disorders, such as obesity.

BACKGROUND OF THE INVENTION

Serotonin (5-HT) neurotransmission plays an important role in numerous physiological processes both in health and in psychiatric disorders. For example, 5-HT has been implicated in the regulation of feeding behavior. 5-HT is believed to work by inducing a feeling of fullness or satiety so eating stops earlier and fewer calories are consumed. It has been shown that a stimulatory action of 5-HT on the 5-HT$_{2C}$ receptor plays an important role in the control of eating and in the anti-obesity effect of d-fenfluramine. As the 5-HT$_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective 5-HT$_{2C}$ receptor agonist can be a more effective and safe anti-obesity agent. Also, 5-HT$_{2C}$ knockout mice are overweight with cognitive impairment and susceptibility to seizure. Thus, the 5-HT$_{2C}$ receptor is recognized as a well-accepted receptor target for the treatment of obesity, psychiatric, and other disorders. See, for example, Halford et al., *Serotonergic Drugs Effects on Appetite Expression and Use for the Treatment of Obesity*, Drugs 2007; 67 (1): 27-55; Naughton et al., *A Review Of The Role Of Serotonin Receptors In Psychiatric Disorders*. Human Psychopharmacology (2000), 15(6), 397-415.

(R)-8-Chloro-1-methyl-2,3,4,5-tetrahydro-1H-3-benzazepine hydrochloride (lorcaserin hydrochloride) is an agonist of the 5-HT$_{2C}$ receptor and shows effectiveness at reducing obesity in animal models and humans.

Various synthetic routes to (R)-8-chloro-1-methyl-2,3,4,5-tetrahydro-1H-3-benzazepine, its related salts, enantiomers, crystalline forms, and intermediates, have been reported in WO 2003/086306, WO 2005/019179, WO 2006/069363, WO 2007/120517, WO 2008/070111, and WO 2009/111004 each of which is incorporated herein by reference in its entirety.

Combinations of lorcaserin with other agents, including without limitation, phentermine, and uses of such combinations in therapy are described in WO 2006/071740, which is incorporated herein by reference in its entirety.

In December 2009, Arena Pharmaceuticals, Inc. submitted a New Drug Application, or NDA, for lorcaserin to the FDA. The NDA submission is based on an extensive data package from lorcaserin's clinical development program that includes 18 clinical trials totaling 8,576 patients. The pivotal phase 3 clinical trial program evaluated nearly 7,200 patients treated for up to two years, and showed that lorcaserin consistently produced significant weight loss with excellent tolerability. About two-thirds of patients achieved at least 5% weight loss and over one-third achieved at least 10% weight loss. On average, patients lost 17 to 18 pounds or about 8% of their weight. Secondary endpoints, including body composition, lipids, cardiovascular risk factors and glycemic parameters improved compared to placebo. In addition, heart rate and blood pressure went down. Lorcaserin did not increase the risk of cardiac valvulopathy. Lorcaserin improved quality of life, and there was no signal for depression or suicidal ideation. The only adverse event that exceeded the placebo rate by 5% was generally mild or moderate, transient headache. Based on a normal BMI of 25, patients in the first phase 3 trial lost about one-third of their excess body weight. The average weight loss was 35 pounds or 16% of body weight for the top quartile of patients in the second phase 3 trial.

In view of the growing demand for compounds useful in the treatment of disorders related to the 5-HT$_{2C}$ receptor, (R)-8-chloro-1-methyl-2,3,4,5-tetrahydro-1H-3-benzazepine has emerged has an important new compound. Accordingly, new and more efficient routes leading to intermediates useful in the preparation of (R)-8-chloro-1-methyl-2,3,4,5-tetrahydro-1H-3-benzazepine are needed. The processes and compounds described herein help meet these and other needs.

SUMMARY OF THE INVENTION

The processes and intermediates of the present invention are useful in preparing 2-chloro-N-(4-chlorophenethyl)propan-1-amine and salts thereof (Compound VI):

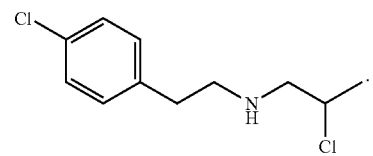

Compound VI is disclosed in WO 2005/019179. It is useful in the preparation (R)-8-chloro-1-methyl-2,3,4,5-tetrahydro-1H-3-benzazepine (Compound I), which is disclosed in WO 2003/086306 and is useful for treating 5-HT$_{2C}$ receptor-associated disorders, such as, obesity.

One aspect of the present invention pertains to processes for preparing a compound selected from: 2-chloro-N-(4-chlorophenethyl)propan-1-amine (Compound VI), which has the following structure:

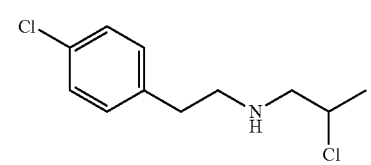

and salts thereof; comprising the following steps:
(a) reacting 2-(4-chlorophenyl)ethanol (Compound II):

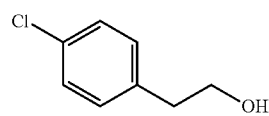

or a salt thereof, with a first chlorinating agent to form 1-chloro-4-(2-chloroethyl)benzene (Compound III):

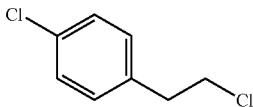

(b) reacting the 1-chloro-4-(2-chloroethyl)benzene (Compound III) with 1-aminopropan-2-ol (Compound IV):

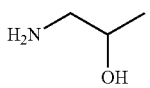

or a salt thereof, to form 1-(4-chlorophenethylamino)propan-2-ol (Compound V):

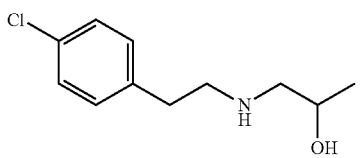

or a salt thereof; and
(c) reacting the 1-(4-chlorophenethylamino)propan-2-ol (Compound V) or a salt thereof, with a second chlorinating agent to form the compound selected from: 2-chloro-N-(4-chlorophenethyl)propan-1-amine (Compound VI) and salts thereof.

One aspect of the present invention pertains to processes for preparing a compound selected from: 2-chloro-N-(4-chlorophenethyl)propan-1-amine (Compound VI):

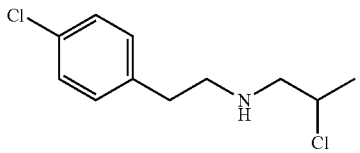

and salts thereof, comprising reacting 1-(4-chlorophenethylamino)propan-2-ol (Compound V):

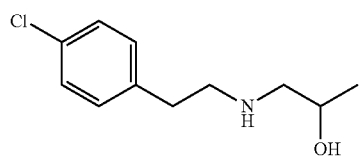

or a salt thereof, with a second chlorinating agent to form the compound selected from: 2-chloro-N-(4-chlorophenethyl)propan-1-amine (Compound VI) and salts thereof; wherein the reacting 1-(4-chlorophenethylamino)propan-2-ol (Compound V) or a salt thereof, with a second chlorinating agent, is carried out in the presence of a first halogenated solvent, wherein the first halogenated solvent comprises chlorobenzene.

One aspect of the present invention pertains to processes for preparing a compound selected from: 2-chloro-N-(4-chlorophenethyl)propan-1-amine (Compound VI):

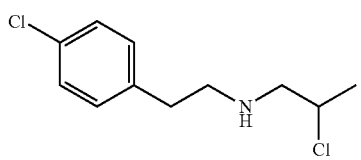

and salts thereof, comprising reacting 1-(4-chlorophenethylamino)propan-2-ol (Compound V):

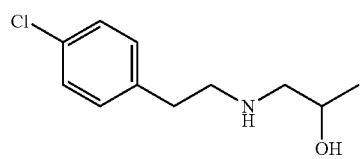

or a salt thereof, with a second chlorinating agent to form a compound selected from: 2-chloro-N-(4-chlorophenethyl)propan-1-amine (Compound VI) and salts thereof; wherein the reacting comprises formation of a reaction mixture by addition of the 1-(4-chlorophenethylamino)propan-2-ol (Compound V) to the second chlorinating agent.

One aspect of the present invention pertains to processes for preparing a compound selected from: 2-chloro-N-(4-chlorophenethyl)propan-1-amine (Compound VI):

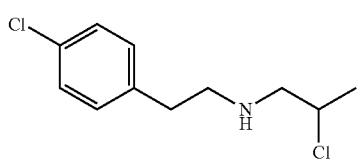

and salts thereof, comprising reacting 1-(4-chlorophenethylamino)propan-2-ol (Compound V):

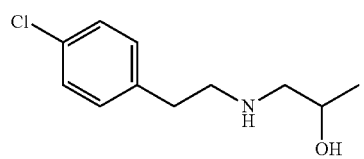

or a salt thereof, with a second chlorinating agent to form a compound selected from: 2-chloro-N-(4-chlorophenethyl)propan-1-amine (Compound VI) and salts thereof; wherein the reacting comprises formation of a reaction mixture by addition of the second chlorinating agent to the 1-(4-chlorophenethylamino)propan-2-ol (Compound V) at a rate such that the reaction mixture is substantially free of solid precipitates during the addition.

One aspect of the present invention pertains to processes for preparing 1-(4-chlorophenethylamino)propan-2-ol (Compound V):

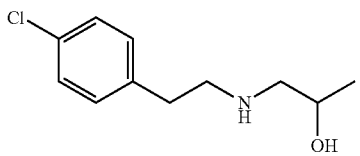

V or a salt thereof, comprising reacting 1-chloro-4-(2-chloroethyl)benzene (Compound III):

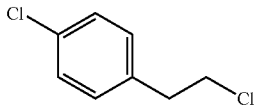

III with 1-aminopropan-2-ol (Compound IV):

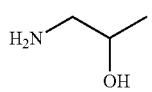

IV or a salt thereof, to form 1-(4-chlorophenethylamino)propan-2-ol (Compound V) or a salt thereof.

One aspect of the present invention pertains to processes for preparing 1-chloro-4-(2-chloroethyl)benzene (Compound III):

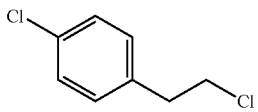

III comprising reacting 2-(4-chlorophenyl)ethanol (Compound II):

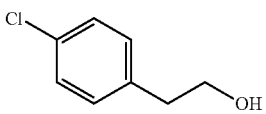

II or a salt thereof, with thionyl chloride to form the 1-chloro-4-(2-chloroethyl)benzene (Compound III); provided the reacting is carried out in the substantial absence of pyridine.

One aspect of the present invention pertains to compounds selected from: 2-chloro-N-(4-chlorophenethyl)propan-1-amine (Compound VI), and salts thereof, wherein a solution of the compound in methanol with a concentration of 40 mg/mL, has a maximum UV absorbance of about 0.1 AU or less between about 300 nm and about 350 nm, wherein the compound is singly-crystallized.

One aspect of the present invention pertains to compounds selected from: 2-chloro-N-(4-chlorophenethyl)propan-1-amine (Compound VI), and salts thereof, prepared by a process of the present invention, wherein a solution of the compound in methanol with a concentration of 40 mg/mL, has a maximum UV absorbance of about 0.100 AU or less between about 300 nm and about 350 nm, and wherein the process does not comprise recrystallization of the compound selected from: 2-chloro-N-(4-chlorophenethyl)propan-1-amine (Compound VI), and salts thereof.

The present invention provides a process for preparing a compound of Formula I:

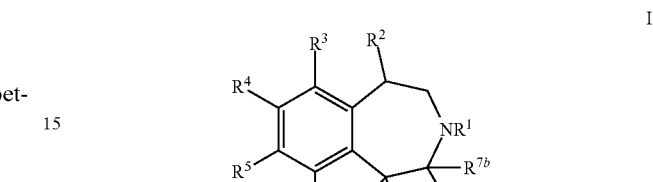

I or salt form thereof,
wherein
$R^1$ is H or $C_1$-$C_8$ alkyl;
$R^2$ is $C_1$-$C_8$ alkyl, —$CH_2$—O—($C_1$-$C_8$ alkyl), C(O)O—($C_1$-$C_8$ alkyl), —C(O)NH—($C_1$-$C_8$ alkyl), OH, $C_1$-$C_4$ haloalkyl, or $CH_2OH$;
$R^3$, $R^4$, $R^5$, and $R^6$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, hydroxy, mercapto, $OR^9$, $SR^9$, alkoxyalkyl, C(O)-alkyl, C(O)O-alkyl, C(O)NH-alkyl, hydroxyalkyl, $NR^{10}R^{11}$, CN, $NO_2$, heterocycloalkyl, aryl, or heteroaryl, wherein said aryl and heteroaryl can be substituted with one or more substituents selected from $C_1$-$C_8$ alkyl, halo, $C_1$-$C_8$ haloalkyl, and alkoxy; or $R^4$ and $R^5$ together with the atoms to which they are attached form a 5- or 6-member heterocyclic ring having one O atom;
$R^{7a}$ and $R^{7b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{7a}$ and $R^{7b}$ together with the carbon atom to which they are attached form a $C_3$-$C_7$ cycloalkyl group;
$R^{8a}$ and $R^{8b}$ are each, independently, H, halo, $C_1$-$C_8$ alkyl, $C_2$-$C_8$ alkenyl, $C_2$-$C_8$ alkynyl, $C_3$-$C_7$ cycloalkyl, $C_1$-$C_8$ haloalkyl, alkoxyalkyl, hydroxy, C(O)-alkyl, C(O)O-alkyl, C(O)NH-alkyl, or hydroxyalkyl, or $R^{8a}$ and $R^{8b}$ together with the carbon atom to which they are attached form a $C_3$-$C_7$ cycloalkyl group;
$R^9$ is H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl; and
$R^{10}$ and $R^{11}$ are each, independently, H, $C_1$-$C_8$ alkyl, $C_1$-$C_8$ alkenyl, $C_1$-$C_8$ alkynyl, $C_3$-$C_7$ cycloalkyl, $C_1$-$C_8$ haloalkyl, aralkyl, aryl, heteroaryl, heteroarylalkyl, or allyl, or $R^{10}$ and $R^{11}$ together with the N atom to which they are attached form a heterocyclic ring;
comprising reacting a compound of Formula IIIa:

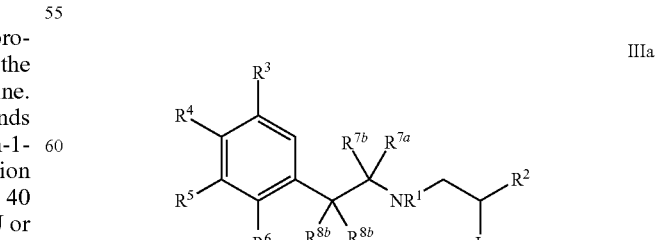

IIIa with a cyclizing reagent for a time and under conditions suitable for forming the compound of Formula I.

In some embodiments, L of the compound of Formula IIIa is halo. In further embodiments, L of the compound of Formula IIIa is Br or Cl.

In some embodiments, the cyclizing reagent includes a Lewis acid, such as, for example, a $C_1$-$C_8$ alkyl aluminum halide (e.g., methyl aluminum chloride, ethyl aluminum chloride, etc.), a $C_2$-$C_{16}$ dialkyl aluminum halide (e.g., dimethyl aluminum chloride, diethyl aluminum chloride, etc.), trialkylaluminum, $AlCl_3$, or $AlBr_3$. Other suitable cyclizing reagents include acids such as sulfuric acid.

Cyclization can be carried out in the absence of solvent or in the presence of solvent. Suitable solvents include nonpolar or weakly polar solvents such as decahydronaphthalene or 1,2-dichlorobenzene. Other suitable solvents include haloalkanes and other halogenated aromatics such as 1,3-dichlorobenzene and 1,4-dichlorobenzene.

The cyclizing reagent can be provided in an amount suitable for maximizing the yield of the cyclized product. In some embodiments, the cyclizing reagent can be provided in molar excess relative to the amount of compound of Formula IIIa. Example molar ratios of cyclizing reagent to compound of Formula IIIa include about 2:1, about 3:1, about 5:1, or about 10:1. In some embodiments, the molar ratio is about 3:1.

In further embodiments, cyclization is carried out at elevated temperature such as at about 80 to about 160° C. In some embodiments, cyclization is carried out at about 140° C. The cyclization reaction can be monitored by LC/MS. Duration to completion can be about 10 minutes to about 24 hours. In some embodiments, reaction duration is from about 3 hours to about 15 hours.

In some embodiments, the yield for the cyclization reaction (based on amount of compound of Formula IIIa), is greater than about 40%, about 50%, about 60%, about 70%, about 80%, or about 90%.

In further embodiments, the present invention provides a method of resolving a mixture of compounds of Formulas Ia and Ib:

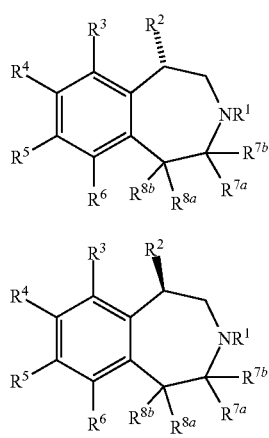

by contacting the mixture of compounds with a chiral resolving acid enriched in one stereoisomer (e.g., ee greater than about 50%, about 75%, about 90% or about 95%) to form chiral resolving acid salts of the compounds of the mixture, and then precipitating the chiral resolving acid salts. The resulting precipitate is typically enriched in the chiral resolving acid salt of one of the compounds of Formulas Ia or Ib (e.g., ee >50%). In some embodiments, the precipitate is enriched in the chiral resolving acid salt form of the compound of Formula Ia. In some embodiments, the precipitate is enriched in the chiral resolving acid salt form of the compound of Formula Ib. In further embodiments, the chiral resolving acid is a stereoisomer of toluoyl tartaric acid, camphoric acid, ketogulonic acid, or tartaric acid. In further embodiments, the chiral resolving acid is a stereoisomer of tartaric acid such as L-(+)-tartaric acid.

Contacting of compounds with a chiral resolving acid can be carried out in solution. Suitable solvents support dissolution of both the chiral resolving acid and the compounds of Formulas Ia and Ib. Some example solvents include polar solvents or water-miscible solvents such as alcohols (e.g., methanol, ethanol, isopropanol, t-butanol, and the like), isopropylacetate, water, and mixtures thereof. In further embodiments, the solvent contains a mixture of t-butanol and water. Some example mixtures include about 5-25% water and about 75-95% t-butanol. In some embodiments, the solvent contains about 8-12% water and about 88-92% of t-butanol.

Precipitate containing the chiral resolving acid salt forms can be formed by precipitation from any suitable solvent which dissolves the salts such as the solvent in which contacting was carried out. Precipitation can be induced by any method known in the art such as by heating a solution containing the mixture of salts followed by cooling. Precipitate can be separated from the solvent by, for example, filtration. Enrichment of the precipitate in one chiral salt over the other can be characterized by an enantiomeric excess (ee) of greater than about 50%, about 60%, about 70%, about 80%, about 90%, about 95%, about 98%, or about 99%. In some embodiments, ee is greater than about 80%. Precipitation can be repeated one or more times to increase the proportion of a chiral salt in the precipitate by re-dissolving and re-precipitating previously obtained precipitate.

DETAILED DESCRIPTION

Figure 1:
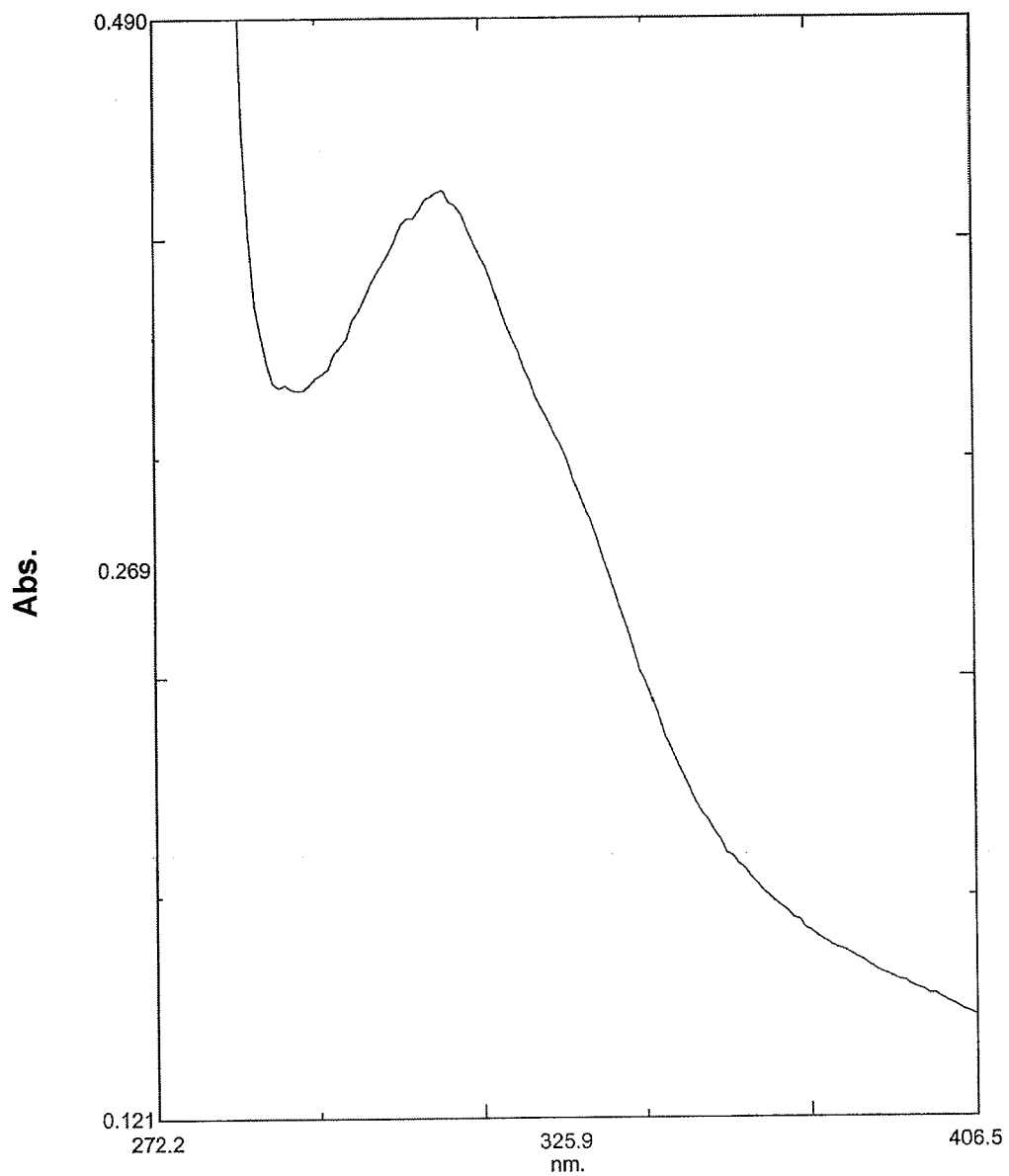
FIG. 1 shows the ultraviolet spectrum of 2-chloro-N-(4-chlorophenethyl)propan-1-amine (Compound VI) hydrochloride prepared according to the procedure described in Example 1, Method 3.

The present disclosure includes all isotopes of atoms occurring in the present process intermediates. Isotopes include those atoms having the same atomic number but different mass numbers. By way of general example, and without limitation, isotopes of hydrogen include $^2H$ (deuterium) and $^3H$ (tritium). Isotopes of carbon include $^{13}C$ and $^{14}C$.

The processes and intermediates of the present invention are useful in the preparation of the therapeutic agent (R)-8-chloro-1-methyl-2,3,4,5-tetrahydro-1H-3-benzazepine, including, salts and crystalline forms thereof. The compound (R)-8-chloro-1-methyl-2,3,4,5-tetrahydro-1H-3-benzazepine, including, salts and crystalline forms are disclosed in PCT patent publications, WO 2003/086306 and WO 2006/069363.

Certain processes for the preparation of (R)-8-chloro-1-methyl-2,3,4,5-tetrahydro-1H-3-benzazepine and salts thereof are disclosed in PCT patent publications, WO 2005/019179 and WO 2007/120517, WO 2008/070111, and WO 2009/111004.

Intermediates useful in the preparation of (R)-8-chloro-1-methyl-2,3,4,5-tetrahydro-1H-3-benzazepine, HCl salts, hydrate, solvates and crystal forms thereof, include 1-chloro-4-(2-chloroethyl)benzene, 1-(4-chlorophenethylamino)propan-2-ol, and 2-chloro-N-(4-chlorophenethyl)propan-1-amine and salts thereof. Several improvements and advantages have now been discovered for the preparation of each as described herein.

Example processes and intermediates of the present invention are provided below in Scheme II.

Scheme II

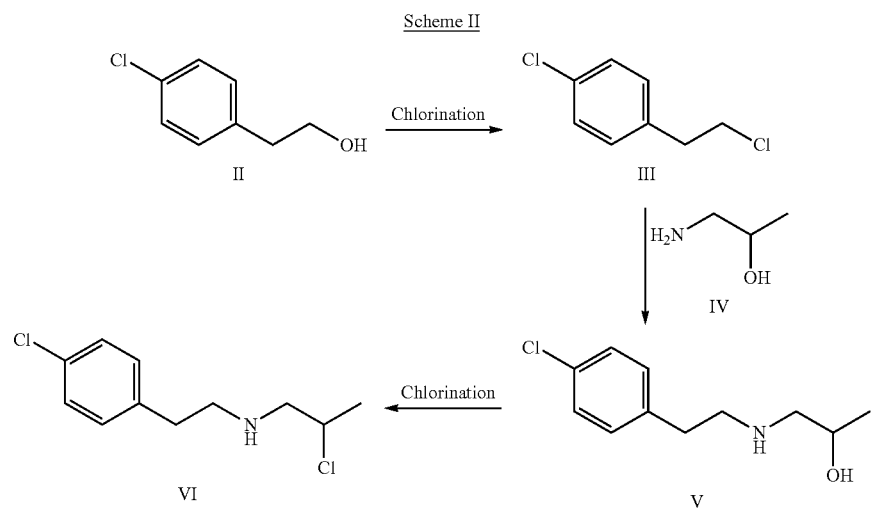

Definitions

For clarity and consistency, the following definitions will be used throughout this patent document.

The term "agonists" is intended to mean moieties that interact and activate a receptor, such as the 5-HT$_{2C}$ serotonin receptor, and initiate a physiological or pharmacological response characteristic of that receptor, for example, moieties that activate the intracellular response upon binding to the receptor, or enhance GTP binding to membranes.

The term "hydrate" as used herein means a compound, including but not limited to a pharmaceutically acceptable salt of a compound, that further includes a stoichiometric or non-stoichiometric amount of water bound by non-covalent intermolecular forces.

The term "individual" is intended to mean any animal, including mammals, preferably mice, rats, other rodents, rabbits, dogs, cats, swine, cattle, sheep, horses, or primates and most preferably humans.

The term "solvate" as used herein means a compound, including but not limited to a pharmaceutically acceptable salt of a compound, that further includes a stoichiometric or non-stoichiometric amount of a solvent bound by non-covalent intermolecular forces. Preferred solvents are volatile, non-toxic, and/or acceptable for administration to humans in trace amounts.

Processes of the Invention

The present invention is directed, inter alia, to processes and intermediates useful in the preparation of 2-chloro-N-(4-chlorophenethyl)propan-1-amine (Compound VI). Compound VI, is useful in the preparation of (R)-8-chloro-1-methyl-2,3,4,5-tetrahydro-1H-3-benzazepine, a serotonin (5-HT) receptor modulator that is useful in the treatment of central nervous system disorders, such as obesity.

One aspect of the present invention pertains to processes, such as those exemplified by Scheme II (supra), that involve Compounds II, III, IV, V, and VI.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

First Chlorinating Step One aspect of the present invention pertains to processes for preparing 1-chloro-4-(2-chloroethyl)benzene (Compound III):

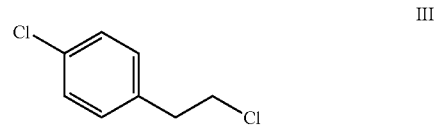

comprising reacting 2-(4-chlorophenyl)ethanol (Compound II):

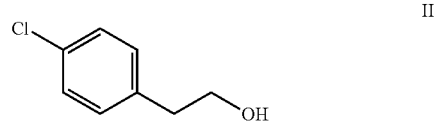

or a salt thereof, with a first chlorinating agent to form 1-chloro-4-(2-chloroethyl)benzene (Compound III).

In some embodiments, the first chlorinating agent comprises: thionyl chloride, oxalyl chloride, methanesulfonyl chloride, benzenesulfonyl chloride, toluenesulfonyl chloride, phosphorous trichloride, phosphorous pentachloride, phosphorous oxychloride, chlorine, hydrogen chloride, carbon tetrachloride, hexachloroethane, trichloroacetonitrile, hexachloroacetone, isopropyl trichloroacetate, ethyl trichloroacetate, trichloroacetamide, trichloroacetanilide, N-chlorosuccinimide, tetrahexylammonium chloride, 2,2,4,6-tetrachloro-2,2-dihydro-1,3,5,2-triazaphosphorine, or 2,4,6-trichloro-1,3,5-triazine.

In some embodiments, the first chlorinating agent comprises: thionyl chloride, oxalyl chloride, methanesulfonyl chloride, benzenesulfonyl chloride, toluenesulfonyl chloride, phosphorous trichloride, phosphorous pentachloride, phosphorous oxychloride, chlorine, hydrogen chloride, carbon tetrachloride, hexachloroethane, trichloroacetonitrile, hexachloroacetone, isopropyl trichloroacetate, ethyl trichloroacetate, trichloroacetamide, trichloroacetanilide, N-chlorosuccinimide, tetrahexylammonium chloride, 2,2,4,6-tetrachloro-2,2-dihydro-1,3,5,2-triazaphosphorine, or 2,4,6-trichloro-1,3,5-triazine, or mixtures thereof.

In some embodiments, the first chlorinating agent comprises thionyl chloride.

In some embodiments, the first chlorinating agent comprises thionyl chloride and the reacting 2-(4-chlorophenyl)ethanol or a salt thereof, with the first chlorinating agent, is performed in the substantial absence of pyridine.

In some embodiments, the first chlorinating agent comprises oxalyl chloride.

In some embodiments, the first chlorinating agent comprises methanesulfonyl chloride.

In some embodiments, the first chlorinating agent comprises benzenesulfonyl chloride.

In some embodiments, the first chlorinating agent comprises toluenesulfonyl chloride.

In some embodiments, the first chlorinating agent comprises phosphorous trichloride.

In some embodiments, the first chlorinating agent comprises phosphorous pentachloride.

In some embodiments, the first chlorinating agent comprises phosphorous oxychloride.

In some embodiments, the first chlorinating agent comprises chlorine.

In some embodiments, the first chlorinating agent comprises hydrogen chloride.

In some embodiments, the first chlorinating agent comprises carbon tetrachloride.

In some embodiments, the first chlorinating agent comprises hexachloroethane.

In some embodiments, the first chlorinating agent comprises trichloroacetonitrile.

In some embodiments, the first chlorinating agent comprises hexachloroacetone.

In some embodiments, the first chlorinating agent comprises isopropyl trichloroacetate.

In some embodiments, the first chlorinating agent comprises ethyl trichloroacetate.

In some embodiments, the first chlorinating agent comprises trichloroacetamide.

In some embodiments, the first chlorinating agent comprises trichloroacetanilide.

In some embodiments, the first chlorinating agent comprises N-chlorosuccinimide.

In some embodiments, the first chlorinating agent comprises tetrahexylammonium chloride.

In some embodiments, the first chlorinating agent comprises 2,2,4,6-tetrachloro-2,2-dihydro-1,3,5,2-triazaphosphorine.

In some embodiments, the first chlorinating agent comprises 2,4,6-trichloro-1,3,5-triazine.

In some embodiments, the reacting 2-(4-chlorophenyl)ethanol or a salt thereof, with the first chlorinating agent, is performed in the substantial absence of solvent.

In some embodiments, the reacting 2-(4-chlorophenyl)ethanol or a salt thereof, with the first chlorinating agent, is performed in the presence of a first aprotic solvent.

In some embodiments, the reacting 2-(4-chlorophenyl)ethanol or a salt thereof, with the first chlorinating agent, is performed in the presence of toluene.

In some embodiments, the reacting 2-(4-chlorophenyl)ethanol or a salt thereof, with the first chlorinating agent, is performed in the presence of a first aprotic solvent, wherein the first aprotic solvent comprises toluene.

In some embodiments, the reacting 2-(4-chlorophenyl)ethanol or a salt thereof, with the first chlorinating agent, is performed in the presence of a first aprotic solvent, wherein the first aprotic solvent comprises an amide.

In some embodiments, the reacting 2-(4-chlorophenyl)ethanol or a salt thereof, with the first chlorinating agent, is performed in the presence of a first aprotic solvent, wherein the first aprotic solvent comprises N,N-dimethylformamide.

In some embodiments, the reacting 2-(4-chlorophenyl)ethanol or a salt thereof, with the first chlorinating agent, is performed in the presence of a first aprotic solvent, wherein the first aprotic solvent comprises N,N-dimethylacetamide.

In some embodiments, the reacting 2-(4-chlorophenyl)ethanol or a salt thereof, with the first chlorinating agent, is performed at a temperature of about 0° C. to about 100° C.

In some embodiments, the reacting 2-(4-chlorophenyl)ethanol or a salt thereof, with the first chlorinating agent, is performed at a temperature of about 25° C. to about 100° C.

In some embodiments, the reacting 2-(4-chlorophenyl)ethanol or a salt thereof, with the first chlorinating agent, is performed at a temperature of about 40° C. to about 85° C.

In some embodiments, the reacting 2-(4-chlorophenyl)ethanol or a salt thereof, with the first chlorinating agent, is performed at a temperature of about 50° C. to about 75° C.

In some embodiments, the reacting 2-(4-chlorophenyl)ethanol or a salt thereof, with the first chlorinating agent, is performed at a temperature of about 60° C. to about 65° C.

In some embodiments, the molar ratio of the first chlorinating agent and the 2-(4-chlorophenyliethanol or a salt thereof is about 10:1 to about 1:1.

In some embodiments, the molar ratio of the first chlorinating agent and the 2-(4-chlorophenyliethanol or a salt thereof is about 4:1 to about 1:1.

In some embodiments, the molar ratio of the first chlorinating agent and the 2-(4-chlorophenyliethanol or a salt thereof is about 2:1 to about 1:1.

In some embodiments, the molar ratio of the first chlorinating agent and the 2-(4-chlorophenyliethanol or a salt thereof is about 1.2:1 to about 1:1.

In some embodiments, the reacting 2-(4-chlorophenyl)ethanol or a salt thereof, with the first chlorinating agent, is performed in the presence of a first catalyst.

In some embodiments, the first catalyst comprises an amide.

In some embodiments, the first catalyst comprises N,N-dimethylformamide.

In some embodiments, the first catalyst comprises N,N-dimethylacetamide.

In some embodiments, the first catalyst comprises an amine.

In some embodiments, the first catalyst comprises a tri-$C_1$-$C_6$ alkyl amine.

In some embodiments, the first catalyst comprises triethylamine.

In some embodiments, the reacting 2-(4-chlorophenyl)ethanol or a salt thereof, with the first chlorinating agent, is performed in the presence of a first catalyst, wherein the first catalyst comprises N,N-dimethylformamide.

In some embodiments, the molar ratio of the 2-(4-chlorophenyl)ethanol or a salt thereof and the first catalyst is about 100:1 to about 1:1.

In some embodiments, the molar ratio of the 2-(4-chlorophenyl)ethanol or a salt thereof and the first catalyst is about 25:1 to about 5:1.

In some embodiments, the molar ratio of the 2-(4-chlorophenyl)ethanol or a salt thereof and the first catalyst is about 7:1 to about 6:1.

In some embodiments, the molar ratio of the 2-(4-chlorophenyl)ethanol or a salt thereof and the first catalyst is about 20:1.

Reacting with 1-Aminopropan-2-ol Step

One aspect of the present invention pertains to processes for preparing 1-(4-chlorophenethylamino)propan-2-ol (Compound V):

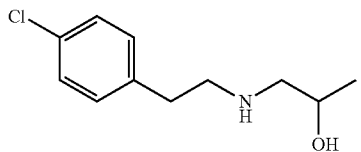

or a salt thereof, comprising reacting 1-chloro-4-(2-chloroethyl)benzene (Compound III):

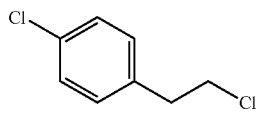

with 1-aminopropan-2-ol (Compound IV):

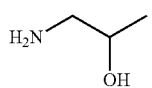

or a salt thereof, to form 1-(4-chlorophenethylamino)propan-2-ol (Compound V) or a salt thereof.

In some embodiments, the reacting 1-chloro-4-(2-chloroethyl)benzene with 1-aminopropan-2-ol or a salt thereof, is performed in the substantial absence of solvent.

In some embodiments, the reacting 1-chloro-4-(2-chloroethyl)benzene with 1-aminopropan-2-ol or a salt thereof, is performed in the presence of toluene.

In some embodiments, the reacting 1-chloro-4-(2-chloroethyl)benzene with 1-aminopropan-2-ol or a salt thereof, is performed at a temperature of about 0° C. to about 150° C.

In some embodiments, the reacting 1-chloro-4-(2-chloroethyl)benzene with 1-aminopropan-2-ol or a salt thereof, is performed at a temperature of about 25° C. to about 150° C.

In some embodiments, the reacting 1-chloro-4-(2-chloroethyl)benzene with 1-aminopropan-2-ol or a salt thereof, is performed at a temperature of about 75° C. to about 100° C.

In some embodiments, the reacting 1-chloro-4-(2-chloroethyl)benzene with 1-aminopropan-2-ol or a salt thereof, is performed at a temperature of about 90° C. to about 95° C.

In some embodiments, the molar ratio of the 1-aminopropan-2-ol or a salt thereof and the 1-chloro-4-(2-chloroethyl)benzene is about 20:1 to about 1:1.

In some embodiments, the molar ratio of the 1-aminopropan-2-ol or a salt thereof and the 1-chloro-4-(2-chloroethyl)benzene is about 10:1 to about 2:1.

In some embodiments, the molar ratio of the 1-aminopropan-2-ol or a salt thereof and the 1-chloro-4-(2-chloroethyl)benzene is about 5:1.

One aspect of the present invention pertains to processes for preparing 1-(4-chlorophenethylamino)propan-2-ol (Compound V) or a salt thereof, comprising reacting 1-chloro-4-(2-chloroethyl)benzene (Compound III) with a compound selected from: 1-aminopropan-2-ol, 5-methyloxazolidin-2-one, and 2,2,5-trimethyloxazolidine, or a salt thereof, to form 1-(4-chlorophenethylamino)propan-2-ol (Compound V) or a salt thereof.

In some embodiments, the reacting 1-chloro-4-(2-chloroethyl)benzene with a compound selected from: 1-aminopropan-2-ol, 5-methyloxazolidin-2-one, and 2,2,5-trimethyloxazolidine, or a salt thereof, is performed in the substantial absence of solvent.

In some embodiments, the reacting 1-chloro-4-(2-chloroethyl)benzene with a compound selected from: 1-aminopropan-2-ol, 5-methyloxazolidin-2-one, and 2,2,5-trimethyloxazolidine, or a salt thereof, is performed at a temperature of about 0° C. to about 150° C.

In some embodiments, the reacting 1-chloro-4-(2-chloroethyl)benzene with a compound selected from: 1-aminopropan-2-ol, 5-methyloxazolidin-2-one, and 2,2,5-trimethyloxazolidine, or a salt thereof, is performed at a temperature of about 25° C. to about 150° C.

In some embodiments, the reacting 1-chloro-4-(2-chloroethyl)benzene with a compound selected from: 1-aminopropan-2-ol, 5-methyloxazolidin-2-one, and 2,2,5-trimethyloxazolidine, or a salt thereof, is performed at a temperature of about 75° C. to about 100° C.

In some embodiments, the reacting 1-chloro-4-(2-chloroethyl)benzene with a compound selected from: 1-aminopropan-2-ol, 5-methyloxazolidin-2-one, and 2,2,5-trimethyloxazolidine, or a salt thereof, is performed at a temperature of about 90° C. to about 95° C.

In some embodiments, the molar ratio of the compound selected from: 1-aminopropan-2-ol, 5-methyloxazolidin-2-one, and 2,2,5-trimethyloxazolidine, or a salt thereof and the 1-chloro-4-(2-chloroethyl)benzene is about 20:1 to about 1:1.

In some embodiments, the molar ratio of the compound selected from: 1-aminopropan-2-ol, 5-methyloxazolidin-2-one, and 2,2,5-trimethyloxazolidine, or a salt thereof and the 1-chloro-4-(2-chloroethyl)benzene is about 10:1 to about 2:1.

In some embodiments, the molar ratio of the compound selected from: 1-aminopropan-2-ol, 5-methyloxazolidin-2-one, and 2,2,5-trimethyloxazolidine, or a salt thereof and the 1-chloro-4-(2-chloroethyl)benzene is about 5:1.

Second Chlorinating Step

One aspect of the present invention pertains to processes for preparing a compound selected from: 2-chloro-N-(4-chlorophenethyl)propan-1-amine (Compound VI):

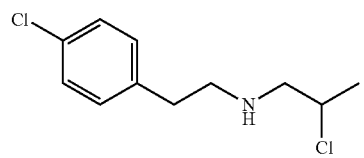

and salts thereof; comprising reacting 1-(4-chlorophenethylamino)propan-2-ol (Compound V):

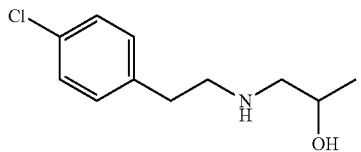

or a salt thereof, with a second chlorinating agent to form the compound selected from: 2-chloro-N-(4-chlorophenethyl)propan-1-amine (Compound VI) and salts thereof.

In some embodiments, the reacting the 1-(4-chlorophenethylamino)propan-2-ol or a salt thereof, with the second chlorinating agent, comprises formation of a reaction mixture by addition of the 1-(4-chlorophenethylamino)propan-2-ol to the second chlorinating agent.

In some embodiments, the reacting the 1-(4-chlorophenethylamino)propan-2-ol or a salt thereof, with the second chlorinating agent, comprises formation of a reaction mixture by addition of the second chlorinating agent to the 1-(4-chlorophenethylamino)propan-2-ol.

In some embodiments, the addition takes about 5 hours or less.

In some embodiments, the addition takes about 4 hours or less.

In some embodiments, the addition takes about 3 hours or less.

In some embodiments, the addition takes about 2 hours or less.

In some embodiments, the addition takes about 1 hour or less.

In some embodiments, the addition takes about 30 minutes or less.

In some embodiments, the addition takes about 25 minutes or less.

In some embodiments, the addition takes about 20 minutes or less.

In some embodiments, the addition takes about 15 minutes or less.

In some embodiments, the addition takes about 10 minutes or less.

In some embodiments, the addition takes about 5 minutes or less.

In some embodiments, the addition takes about 1 minute or less.

In some embodiments, the addition takes about 1 hour.

In some embodiments, the addition takes about 25 minutes.

In some embodiments, the addition takes about 1 minute.

In some embodiments, the addition is performed at a rate such that the reaction mixture is substantially free of solid precipitates during the addition.

One aspect of the present invention pertains to processes for preparing a compound selected from: 2-chloro-N-(4-chlorophenethyl)propan-1-amine (Compound VI):

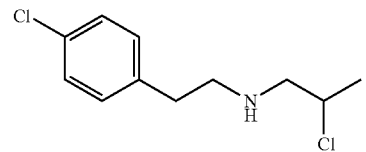

and salts thereof; comprising reacting 1-(4-chlorophenethylamino)propan-2-ol (Compound V):

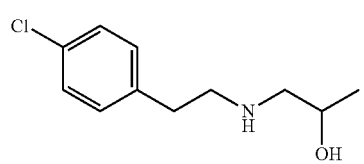

or a salt thereof, with a second chlorinating agent to form the compound selected from: 2-chloro-N-(4-chlorophenethyl)propan-1-amine (Compound VI) and salts thereof or a salt thereof; wherein the reacting 1-(4-chlorophenethylamino)propan-2-ol (Compound V) or a salt thereof, with a second chlorinating agent, is carried out in the presence of a first halogenated solvent.

One aspect of the present invention pertains to processes for preparing a compound selected from: 2-chloro-N-(4-chlorophenethyl)propan-1-amine (Compound VI):

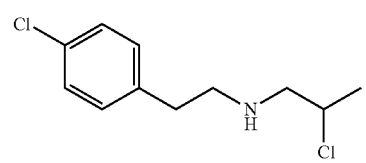

and salts thereof; comprising reacting 1-(4-chlorophenethylamino)propan-2-ol (Compound V):

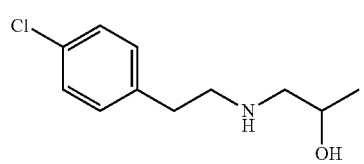

or a salt thereof, with a second chlorinating agent to form the compound selected from: 2-chloro-N-(4-chlorophenethyl)propan-1-amine (Compound VI) and salts thereof; wherein the reacting 1-(4-chlorophenethylamino)propan-2-ol (Compound V) or a salt thereof, with a second chlorinating agent, is carried out in the presence of a first halogenated solvent, wherein the first halogenated solvent comprises chlorobenzene.

One aspect of the present invention pertains to processes for preparing compound selected from: 2-chloro-N-(4-chlorophenethyl)propan-1-amine (Compound VI):

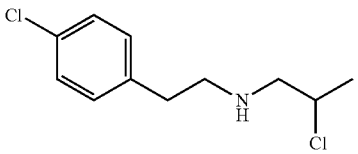

and salts thereof; comprising reacting 1-(4-chlorophenethylamino)propan-2-ol (Compound V):

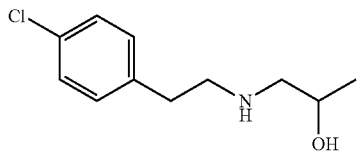

or a salt thereof, with a second chlorinating agent to form the compound selected from: 2-chloro-N-(4-chlorophenethyl)propan-1-amine (Compound VI) and salts thereof; wherein the reacting comprises formation of a reaction mixture by addition of the 1-(4-chlorophenethylamino)propan-2-ol to the second chlorinating agent; or addition of the second chlorinating agent to the 1-(4-chlorophenethylamino)propan-2-ol at a rate such that the reaction mixture is substantially free of solid precipitates during the addition.

In some embodiments, the second chlorinating agent comprises: thionyl chloride, oxalyl chloride, methanesulfonyl chloride, benzenesulfonyl chloride, toluenesulfonyl chloride, phosphorous trichloride, phosphorous pentachloride, phosphorous oxychloride, chlorine, hydrogen chloride, carbon tetrachloride, hexachloroethane, trichloroacetonitrile, hexachloroacetone, isopropyl trichloroacetate, ethyl trichloroacetate, trichloroacetamide, trichloroacetanilide, N-chlorosuccinimide, tetrahexylammonium chloride, 2,2,4,6-tetrachloro-2,2-dihydro-1,3,5,2-triazaphosphorine, or 2,4,6-trichloro-1,3,5-triazine.

In some embodiments, the first chlorinating agent comprises: thionyl chloride, oxalyl chloride, methanesulfonyl chloride, benzenesulfonyl chloride, toluenesulfonyl chloride, phosphorous trichloride, phosphorous pentachloride, phosphorous oxychloride, chlorine, hydrogen chloride, carbon tetrachloride, hexachloroethane, trichloroacetonitrile, hexachloroacetone, isopropyl trichloroacetate, ethyl trichloroacetate, trichloroacetamide, trichloroacetanilide, N-chlorosuccinimide, tetrahexylammonium chloride, 2,2,4,6-tetrachloro-2,2-dihydro-1,3,5,2-triazaphosphorine, or 2,4,6-trichloro-1,3,5-triazine, or mixtures thereof.

In some embodiments, the second chlorinating agent comprises thionyl chloride.

In some embodiments, the second chlorinating agent comprises oxalyl chloride.

In some embodiments, the second chlorinating agent comprises methanesulfonyl chloride.

In some embodiments, the second chlorinating agent comprises benzenesulfonyl chloride.

In some embodiments, the second chlorinating agent comprises toluenesulfonyl chloride.

In some embodiments, the second chlorinating agent comprises phosphorous trichloride.

In some embodiments, the second chlorinating agent comprises phosphorous pentachloride.

In some embodiments, the second chlorinating agent comprises phosphorous oxychloride.

In some embodiments, the second chlorinating agent comprises chlorine.

In some embodiments, the second chlorinating agent comprises hydrogen chloride.

In some embodiments, the second chlorinating agent comprises carbon tetrachloride.

In some embodiments, the second chlorinating agent comprises hexachloroethane.

In some embodiments, the second chlorinating agent comprises trichloroacetonitrile.

In some embodiments, the second chlorinating agent comprises hexachloroacetone.

In some embodiments, the second chlorinating agent comprises isopropyl trichloroacetate.

In some embodiments, the second chlorinating agent comprises ethyl trichloroacetate.

In some embodiments, the second chlorinating agent comprises trichloroacetamide.

In some embodiments, the second chlorinating agent comprises trichloroacetanilide.

In some embodiments, the second chlorinating agent comprises N-chlorosuccinimide.

In some embodiments, the second chlorinating agent comprises tetrahexylammonium chloride.

In some embodiments, the second chlorinating agent comprises 2,2,4,6-tetrachloro-2,2-dihydro-1,3,5,2-triazaphosphorine.

In some embodiments, the second chlorinating agent comprises 2,4,6-trichloro-1,3,5-triazine.

In some embodiments, the reacting 1-(4-chlorophenethylamino)propan-2-ol or a salt thereof, with the second chlorinating agent, is performed in the substantial absence of solvent.

In some embodiments, the reacting 1-(4-chlorophenethylamino)propan-2-ol or a salt thereof, with the second chlorinating agent, is performed in the presence of a first halogenated solvent.

In some embodiments, the reacting 1-(4-chlorophenethylamino)propan-2-ol or a salt thereof, with the second chlorinating agent, is performed in the presence of a first halogenated solvent, wherein the first halogenated solvent comprises chlorobenzene.

In some embodiments, the reacting 1-(4-chlorophenethylamino)propan-2-ol or a salt thereof, with the second chlorinating agent, is performed in the presence of chlorobenzene.

In some embodiments, the reacting 1-(4-chlorophenethylamino)propan-2-ol or a salt thereof, with the second chlorinating agent, is performed in the presence of 1,2-dichlorobenzene.

In some embodiments, the reacting 1-(4-chlorophenethylamino)propan-2-ol or a salt thereof, with the second chlorinating agent, is performed in the presence of a first ether solvent.

In some embodiments, the reacting 1-(4-chlorophenethylamino)propan-2-ol or a salt thereof, with the second chlorinating agent, is performed in the presence of tetrahydrofuran.

In some embodiments, the reacting 1-(4-chlorophenethylamino)propan-2-ol or a salt thereof, with the second chlorinating agent, is performed in the presence of 2-methyltetrahydrofuran.

In some embodiments, the reacting 1-(4-chlorophenethylamino)propan-2-ol or a salt thereof, with the second chlorinating agent, is performed in the substantial absence of an amide catalyst.

In some embodiments, the reacting 1-(4-chlorophenethylamino)propan-2-ol or a salt thereof, with the second chlorinating agent, is performed in the presence of a second aprotic solvent.

In some embodiments, the reacting 1-(4-chlorophenethylamino)propan-2-ol or a salt thereof, with the second chlorinating agent, is performed in the presence of isopropyl acetate.

In some embodiments, the reacting 1-(4-chlorophenethylamino)propan-2-ol or a salt thereof, with the second chlorinating agent, is performed in the presence of xylene.

In some embodiments, the reacting 1-(4-chlorophenethylamino)propan-2-ol or a salt thereof, with the second chlorinating agent, is performed in the presence of toluene.

In some embodiments, the reacting 1-(4-chlorophenethylamino)propan-2-ol or a salt thereof, with the second chlorinating agent, is performed in the presence of a second aprotic solvent, wherein the second aprotic solvent comprises toluene.

In some embodiments, the reacting 1-(4-chlorophenethylamino)propan-2-ol or a salt thereof, with the second chlorinating agent, is performed at a temperature of about 0° C. to about 100° C.

In some embodiments, the reacting 1-(4-chlorophenethylamino)propan-2-ol or a salt thereof, with the second chlorinating agent, is performed at a temperature of about 25° C. to about 100° C.

In some embodiments, the reacting 1-(4-chlorophenethylamino)propan-2-ol or a salt thereof, with the second chlorinating agent, is performed at a temperature of about 40° C. to about 85° C.

In some embodiments, the reacting 1-(4-chlorophenethylamino)propan-2-ol or a salt thereof, with the second chlorinating agent, is performed at a temperature of about 50° C. to about 75° C.

In some embodiments, the reacting 1-(4-chlorophenethylamino)propan-2-ol or a salt thereof, with the second chlorinating agent, is performed at a temperature of about 60° C. to about 65° C.

In some embodiments, the molar ratio of the second chlorinating agent and the 1-(4-chlorophenethylamino)propan-2-ol or a salt thereof is about 10:1 to about 1:1.

In some embodiments, the molar ratio of the second chlorinating agent and the 1-(4-chlorophenethylamino)propan-2-ol or a salt thereof is about 4:1 to about 1:1.

In some embodiments, the molar ratio of the second chlorinating agent and the 1-(4-chlorophenethylamino)propan-2-ol or a salt thereof is about 2:1 to about 1:1.

In some embodiments, the molar ratio of the second chlorinating agent and the 1-(4-chlorophenethylamino)propan-2-ol or a salt thereof is about 1.6:1 to about 1.1:1.

In some embodiments, the molar ratio of the second chlorinating agent and the 1-(4-chlorophenethylamino)propan-2-ol or a salt thereof is about 1.4:1 to about 1.1:1.

In some embodiments, the reacting 1-(4-chlorophenethylamino)propan-2-ol or a salt thereof, with the second chlorinating agent, is performed in the presence of a second catalyst.

In some embodiments, the second catalyst comprises an amide.

In some embodiments, the second catalyst comprises N,N-dimethylformamide.

In some embodiments, the second catalyst comprises N,N-dimethylacetamide.

In some embodiments, the second catalyst comprises an amine.

In some embodiments, the second catalyst comprises a tri-$C_1$-$C_6$ alkyl amine.

In some embodiments, the second catalyst comprises triethylamine.

In some embodiments, the molar ratio of the 1-(4-chlorophenethylamino)propan-2-ol or a salt thereof and the second catalyst is about 100:1 to about 1:1.

In some embodiments, the molar ratio of the 1-(4-chlorophenethylamino)propan-2-ol or a salt thereof and the second catalyst is about 10:1 to about 2:1.

In some embodiments, the molar ratio of the 1-(4-chlorophenethylamino)propan-2-ol or a salt thereof and the second catalyst is about 4:1 to about 3:1.

One aspect of the present invention pertains to compounds selected from: 2-chloro-N-(4-chlorophenethyl)propan-1-amine (Compound VI), and salts thereof, wherein a solution of the compound in methanol with a concentration of 40 mg/mL, has a maximum UV absorbance of about 0.100 AU or less between about 300 nm and about 350 nm, wherein the compound is singly-crystallized.

One aspect of the present invention pertains to compounds selected from: 2-chloro-N-(4-chlorophenethyl)propan-1-amine (Compound VI), and salts thereof, wherein a solution of the compound in methanol with a concentration of 40 mg/mL, has a maximum UV absorbance of about 0.100 AU or less between about 310 nm and about 340 nm, wherein the compound is singly-crystallized.

One aspect of the present invention pertains to compounds selected from: 2-chloro-N-(4-chlorophenethyl)propan-1-amine (Compound VI), and salts thereof, wherein a solution of the compound in methanol with a concentration of 40 mg/mL, has a maximum UV absorbance of about 0.100 AU or less between about 315 nm and about 335 nm, wherein the compound is singly-crystallized.

In some embodiments, the maximum UV absorbance is about 0.090 AU or less.

In some embodiments, the maximum UV absorbance is about 0.080 AU or less.

In some embodiments, the maximum UV absorbance is about 0.070 AU or less.

In some embodiments, the maximum UV absorbance is about 0.060 AU or less.

In some embodiments, the maximum UV absorbance is about 0.050 AU or less.

In some embodiments, the maximum UV absorbance is about 0.040 AU or less.

In some embodiments, the maximum UV absorbance is about 0.030 AU or less.

In some embodiments, the maximum UV absorbance is about 0.020 AU or less.

In some embodiments, the maximum UV absorbance is about 0.010 AU or less.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

In some embodiments, preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis*, 3rd Ed., Wiley & Sons, 1999.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as: carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, 1,2-dichlorobenzene, 1,3-dichlorobenzene, 1,4-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable solvents can include ether solvents, such as: dimethoxymethane, tetrahydrofuran, 2-methyltetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable solvents can include protic solvents, such as: water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, isobutyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable solvents can include aprotic solvents, such as: benzene, cyclohexane, pentane, hexane, toluene, cycloheptane, methylcyclohexane, heptane, ethylbenzene, o, m-, or p-xylene, octane, indane, nonane, naphthalene, tetrahydrofuran, acetonitrile, dimethyl sulfoxide, propionitrile, ethyl formate, methyl acetate, hexachloroacetone, acetone, ethyl methyl ketone, ethyl acetate, isopropyl acetate, n-propyl acetate, isobutyl acetate, sulfolane, 1,3-dimethyl-3,4,5,6-tetrahydro-2(1H)-pyrimidinone, 1,3-dimethyl-2-imidazolidinone, N-methylpyrrolidinone, tetramethylurea, nitromethane, and nitrobenzene, and amides, including but not limited to, N,N-dimethylformamide, N,N-dimethylacetamide, formamide, N-methylacetamide, N-methylformamide, N,N-dimethylpropionamide, and hexamethylphosphoramide. It is understood by a person of ordinary skill in the art that that the term amide refers to the following formula:

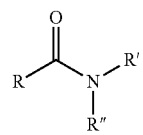

wherein R, R', and R" may be the same or different. In some embodiments, R, R', and R" are independently selected from H and $C_1$-$C_6$ alkyl. In some embodiments, R, R', and R" are independently selected from H and $C_1$-$C_4$ alkyl. In some embodiments, R, R', and R" are independently selected from H and $C_1$-$C_2$ alkyl.

Supercritical carbon dioxide can also be used as a solvent.

The term "in the substantial absence of solvent", it is understood by one of ordinary skill in the art, may refer to a process which is performed neat. In other words, no solvent is added to the reaction mixture prior to or during the course of the process. However, "in the substantial absence of solvent" further contemplates those processes in which the substrates and reagents that comprise the reaction mixture contain residual solvents from the processes by which the substrates and reagents were themselves prepared. In some embodiments, a process "in the substantial absence of solvent" is performed on a reaction mixture which comprises less than 5% solvent by volume. In some embodiments, a process "in the substantial absence of solvent" is performed on a reaction mixture which comprises less than 4% solvent by volume. In some embodiments, a process "in the substantial absence of solvent" is performed on a reaction mixture which comprises less than 3% solvent by volume. In some embodiments, a process "in the substantial absence of solvent" is performed on a reaction mixture which comprises less than 2% solvent by volume. In some embodiments, a process "in the substantial absence of solvent" is performed on a reaction mixture which comprises less than 1% solvent by volume. In some embodiments, a process "in the substantial absence of solvent" is performed on a reaction mixture which comprises less than 0.5% solvent by volume. In some embodiments, a process "in the substantial absence of solvent" is performed on a reaction mixture which comprises less than 0.1% solvent by volume.

In some embodiments, a process "in the substantial absence of pyridine" is performed on a reaction mixture which comprises less than 5% pyridine by volume. In some embodiments, a process "in the substantial absence of pyridine" is performed on a reaction mixture which comprises less than 4% pyridine by volume. In some embodiments, a process "in the substantial absence of pyridine" is performed on a reaction mixture which comprises less than 3% pyridine by volume. In some embodiments, a process "in the substantial absence of pyridine" is performed on a reaction mixture which comprises less than 2% pyridine by volume. In some embodiments, a process "in the substantial absence of pyridine" is performed on a reaction mixture which comprises less than 1% pyridine by volume. In some embodiments, a process "in the substantial absence of pyridine" is performed on a reaction mixture which comprises less than 0.5% pyridine by volume. In some embodiments, a process "in the substantial absence of pyridine" is performed on a reaction mixture which comprises less than 0.1% pyridine by volume.

Certain chlorination reactions described herein may be performed in the presence of certain amides such as, without limitation, N,N-dimethylformamide and N,N-dimethylacetamide. It is understood by a person of ordinary skill in the art, that although amides can function as solvents, the role of the amide in certain chlorination reactions described herein may be primarily that of a catalyst. It is further understood by a person of ordinary skill in the art, that when chlorination reactions are described herein as being performed "in the substantial absence of solvent" such reactions are intended to include those that are performed optionally in the presence of an amide catalyst, but in the substantial absence of a further solvent.

The term "in the substantial absence of an amide catalyst" is understood by one of ordinary skill in the art to refer to processes in which no amide catalyst, for example, N,N-dimethylformamide or N,N-dimethylacetamide is added to the reaction mixture prior to or during the reaction. In some embodiments, a process "in the substantial absence of an amide catalyst" is performed on a reaction mixture which comprises less than 1 mol % of an amide catalyst. In some embodiments, a process "in the substantial absence of an amide catalyst" is performed on a reaction mixture which comprises less than 0.5 mol % of an amide catalyst. In some embodiments, a process "in the substantial absence of an amide catalyst" is performed on a reaction mixture which comprises less than 0.1 mol % of an amide catalyst. In some embodiments, a process "in the substantial absence of an amide catalyst" is performed on a reaction mixture which comprises less than 0.01 mol % of an amide catalyst. In some embodiments, a process "in the substantial absence of an amide catalyst" is performed on a reaction mixture which comprises less than 0.001 mol % of an amide catalyst.

The reactions of the processes described herein can be carried out at appropriate temperatures which can be readily determined by one skilled in the art. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The reactions of the processes described herein can be carried out in air or under an inert atmosphere. Typically, reactions containing reagents or products that are substantially reactive with air can be carried out using air-sensitive synthetic techniques that are well known to one skilled in the art.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, methanesulfonic acid, p-toluene sulfonic acid, benzenesulfonic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, isopropyl, n-butyl, t-butyl, trimethylsilyl and cyclohexyl substituted amides.

The compounds described herein can be asymmetric (e.g., having one or more stereocenters). All stereoisomers, such as enantiomers and diastereomers, are intended unless otherwise indicated. Salts of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis.

The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

Resolution of racemic mixtures of compounds can be carried out by any of numerous methods known in the art. An example method includes fractional recrystallization (for example, diastereomeric salt resolution) using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of β-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

The compounds described herein and salts thereof can also include all isotopes of atoms occurring in the intermediates or final compounds or salts thereof. Isotopes include those atoms having the same atomic number but different mass numbers. For example, isotopes of hydrogen include tritium and deuterium.

Upon carrying out preparation of compounds according to the processes described herein, the usual isolation and purification operations such as concentration, filtration, extraction, solid-phase extraction, recrystallization, chromatography, and the like may be used, to isolate the desired products.

The term "singly-crystallized" is understood by one of ordinary skill in the art to refer to a crystalline reaction product that has not been recrystallized. In some embodiments, a singly-crystallized reaction product is formed in a reaction mixture as a crystalline solid and is then isolated from the reaction mixture by, for example, filtration or centrifugation. An isolated, singly-crystallized reaction product may be analyzed by, for example, UV spectroscopy, without recrystallization. A singly-crystallized reaction product may also be used as a substrate in subsequent chemical reactions without recrystallization.

The term "substantially free of solid precipitates" is understood by one of ordinary skill in the art to refer to a process, or a part thereof, during which the reagents, substrates, products and byproducts do not precipitate from the reaction mixture but remain in solution. In some embodiments, a process "substantially free of solid precipitates" is one in which the reaction mixture comprises less than 50% solid by weight. In some embodiments, a process "substantially free of solid precipitates" is one in which the reaction mixture comprises less than 40% solid by weight. In some embodiments, a process "substantially free of solid precipitates" is one in which the reaction mixture comprises less than 30% solid by weight. In some embodiments, a process "substantially free of solid precipitates" is one in which the reaction mixture comprises less than 20% solid by weight. In some embodiments, a process "substantially free of solid precipitates" is one in which the reaction mixture comprises less than 10% solid by weight. In some embodiments, a process "substantially free of solid precipitates" is one in which the reaction mixture comprises less than 5% solid by weight. In some embodiments, a process "substantially free of solid precipitates" is one in which the reaction mixture comprises less than 2% solid by weight. In some embodiments, a process "substantially free of solid precipitates" is one in which the reaction mixture comprises less than 1% solid by weight. In some embodiments, a process "substantially free of solid precipitates" is one in which the reaction mixture comprises less than 0.5% solid by weight. In some embodiments, a process "substantially free of solid precipitates" is one in which the reaction mixture comprises less than 0.1% solid by weight.

Polymorphism

Polymorphism is the ability of a substance to exist as two or more crystalline phases that have different arrangements and/or conformations of the molecules in the crystal lattice. Polymorphs show the same properties in the liquid or gaseous state but they may behave differently in the solid state.

Besides single-component polymorphs, drugs can also exist as salts and other multicomponent crystalline phases. For example, solvates and hydrates may contain an API host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily.

Recently, polymorph screens of 245 compounds revealed that about 90% of them exhibited multiple solid forms. Overall, approximately half the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, *Crystal Growth & Design* (2007), 7(6), 1007-1026.)

Hydrates and Solvates

Various hydrates and solvates of the compounds described herein and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Accordingly, one aspect of the present invention pertains to methods of administering hydrates and solvates of compounds described herein and/or their pharmaceutical acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Illustrated syntheses of the present invention are shown Scheme I. The syntheses are further illustrated by the following examples. The following examples are provided to further define the invention without, however, limiting the invention to the particulars of these examples. The compounds and salts thereof described herein, supra and infra, are named according to the CS ChemDraw Ultra Version 7.0.1, AutoNom version 2.2, or CS ChemDraw Ultra Version 9.0.7. In certain instances common names are used and it is understood that these common names would be recognized by those skilled in the art.

Chemical shifts of proton nuclear magnetic resonance ($^1$H NMR) spectra are given in parts per million (ppm) with the residual solvent signal used as reference. NMR abbreviations are used as follows: s=singlet, d=doublet, t=triplet, q=quartet, m=multiplet, bs=broad singlet.

LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1

Preparation of
2-Chloro-N-(4-chlorophenethyl)propan-1-amine
(Compound VI) Hydrochloride Method 1

Step A: Preparation of
1-Chloro-4-(2-chloroethyl)benzene (Compound III)

To a 4-L, jacketed glass reactor containing a solution of 2-(4-chlorophenyl)ethanol (Compound II) (591 g, 3774 mmol) dissolved in toluene (1250 mL) and N,N-dimethylformamide (41.4 g, 566 mmol) at 60° C. was charged thionyl chloride (302 mL, 4151 mmol) over 30 min. The addition was exothermic with significant gas evolution. The reaction mixture was stirred for 1.5 h at 60 to 65° C. Reaction conversion was monitored by HPLC and $^1$H NMR. When the amount of 2-(4-chlorophenyl)ethanol remaining was <1 area % by HPLC, the reaction mixture was cooled to 20 to 25° C. Water (1000 mL) was charged to the reactor and the mixture was stirred for 15 min. The aqueous layer was removed and the organic phase was washed twice with saturated sodium bicarbonate solution (1000 mL). Evaporation of the organic phase afforded the title compound as a colorless to yellow oil (641 g, 97% yield, 100 area % by HPLC). $^1$H NMR (400 Hz, CDCl$_3$) δ 3.06 (t, J=7.2 Hz, 2H), 3.72 (t, J=7.2 Hz, 2H), 7.19 (d, J=10 Hz, 2H), 7.32 (d, J=10 Hz, 2H).

Step B: Preparation of 1-(4-Chlorophenethylamino)propan-2-ol (Compound V)

To a 250 mL round-bottomed flask containing a stirring solution of 1-aminopropan-2-ol (Compound IV) (55.1 mL, 714 mmol) at 88° C. was slowly charged 1-chloro-4-(2-chloroethyl)benzene (Compound III) (25.0 g, 143 mmol) while maintaining the temperature below 95° C. The mixture was stirred overnight at 90 to 95° C. and monitored by HPLC. Once the remaining 1-chloro-4-(2-chloroethyl)benzene was <1 area % by HPLC, the solution was allowed to cool to room temperature and a solid precipitated out. The mixture was dissolved in toluene (50 mL) and water (25 mL) at 70° C. and stirred for 15 min. The layers were separated at room temperature and the organic phase was removed. The aqueous phase was extracted with toluene (2×25 mL) at 70° C. The combined organic phases were washed water (2×25 mL) at 70° C. and concentrated under reduced pressure at 60° C. to leave an off-white solid (44.1 g). Toluene (70.5 g) was added and the mixture was stirred at 45° C. to dissolve. Water content was verified to be <0.15% by Karl Fischer titration before continuing to Step C.

Step C: Preparation of 2-Chloro-N-(4-chlorophenethyl)propan-1-amine (Compound VI) Hydrochloride To the toluene solution of 1-(4-chlorophenethylamino)propan-2-ol (Compound V) from Step B was added more toluene (30 mL) and the mixture was stirred at 35 to 45° C. overnight under nitrogen. N,N-Dimethylacetamide (4.01 mL, 42.8 mmol) was added and the mixture was heated to 50° C. Thionyl chloride (13.24 mL, 181 mmol) was added portionwise via syringe over 30 min while maintaining the internal temperature below 65° C. The mixture was stirred at 60 to 65° C. for about 3 h. 2-Propanol (26.1 mL) was slowly charged to the reaction which was then heated to reflux. After about 2 h additional 2-propanol (11 mL) was added. The reaction was then allowed to cool to room temperature and stirred overnight. Next, the reaction was cooled and stirred at 0 to 3° C. for 3.5 h to form a slurry. The slurry was filtered and the filter cake was washed with 2-propanol and dried on the filter under reduced pressure to leave an off-white solid (31.447 g). The cake was then suspended in 2-propanol (100 mL) and the mixture was stirred and heated to reflux. Hydrochloric acid (0.422 mL, 5.14 mmol) was added to the mixture resulting in a pH of 0-1 by pH paper. Stirring at reflux was continued and a thick precipitate formed. 2-Propanol (20 mL) was added and the mixture was stirred at reflux for 1 h. Water (15.2 mL) was added to form a solution which was then allowed to gradually cool to room temperature. The mixture was then further cooled to 0 to 3° C. in an ice bath and stirred at that temperature for 1 h. The resulting slurry was filtered and the filter cake was washed with 2-propanol and dried under reduced pressure at 60° C. to leave a white solid (27.509 g, 71.7%).

Method 2

Step A: Preparation of 1-Chloro-4-(2-chloroethyl)benzene (Compound III)

To a 4-L, jacketed glass reactor containing 2-(4-chlorophenyl)ethanol (Compound II) (501 g, 3199 mmol) and N,N-dimethylformamide (12.4 mL, 160 mmol) at 55° C. was slowly charged thionyl chloride (245 mL, 3359 mmol) over 120 min. The addition was exothermic with significant gas evolution. The reaction mixture was stirred for 2 h at 60 to 61° C. Reaction conversion was monitored by HPLC and $^1$H NMR. When the amount of 2-(4-chlorophenyl)ethanol remaining was <1 area % by HPLC, the reaction mixture was cooled to room temperature. The reaction mixture was placed under reduced pressure at 60° C. on a rotary evaporator to remove unreacted thionyl chloride. The reaction mixture (566 g) containing 1-chloro-4-(2-chloroethyl)benzene and N,N-dimethylformamide was isolated as a dark brown oil (99.52 area % by HPLC). $^1$H NMR (400 Hz, DMSO-d$_6$) δ 3.05 (t, J=6.8 Hz, 2H), 3.87 (t, J=6.8 Hz, 2H), 7.33-7.41 (m, 4H).

Step B: Preparation of 1-(4-Chlorophenethylamino)propan-2-ol (Compound V)

Into a 4-L jacketed reactor, equipped with an overhead stirrer, a thermocouple, a condenser and a nitrogen inlet was charged 1-amino-2-propanol (1094 mL, 14.2 mol). Stirring was commenced and the reactor jacket was heated to 95° C. (84° C. internal temperature). 1-Chloro-4-(2-chloroethyl)benzene (~496 g, 2.833 mol) (501 g of the mixture containing N,N-dimethylformamide from Step A) was added dropwise over ~80 min at an internal temperature of 84 to 99° C. On completion of the addition the reaction was stirred at 90 to 95° C. for 2 h and then cooled to 85° C. Water (500 mL) and toluene (1 L) were added while maintaining the internal temperature at 70 to 75° C. Stirring was continued at that temperature for another 15 min and then stirring was discontinued and the phases were allowed to separate at 70 to 75° C. The aqueous phase was extracted with toluene (2×500 mL) at 70 to 75° C. The organic phases were combined, cooled to 50° C. and stirred at that temperature overnight. The solution was then heated to 60° C., washed with water (500 mL) and concentrated under reduced pressure at 58 to 65° C. After approximately 650 mL of distillate had been removed, fresh toluene (650 mL) was added. The water content of the resulting solution was determined to be 0.0854% by Karl Fischer titration and the solution was immediately carried forward to Step C.

Step C: Preparation of 2-Chloro-N-(4-chlorophenethyl)propan-1-amine (Compound VI) Hydrochloride To the toluene solution of 1-(4-chlorophenethylamino)propan-2-ol (Compound V) from Step B was added more toluene (500 mL) and the mixture was cooled to 50° C. and stirred under nitrogen for 1 h. N,N-Dimethylacetamide (80 mL, 850 mmol) was added and the mixture was heated to 50° C. Thionyl chloride (428 g, 3.598 mmol) was added portionwise via syringe over 3 h while maintaining the internal temperature below 65° C. On completion of the addition the mixture was stirred at 60 to 61° C. for about 2.5 h. Isopropanol (517 mL) was added at 55 to 63° C. and then the mixture was heated to reflux. After stirring at reflux for 1.5 h the mixture was cooled slowly to 0° C. and stirred overnight. The slurry was filtered and the filter cake was washed with 2-propanol and dried on the filter under reduced pressure to leave an off-white solid (607 g).

A portion of the cake (35 g) was suspended in 2-propanol (100 mL) and the mixture was stirred and heated to reflux. Concentrated hydrochloric acid (0.5 mL) was added to the mixture resulting in a pH of 1-2 by pH paper. A thick precipitate formed and the mixture was stirred at reflux for 2 h. Water (14.5 mL) was added to form a solution which was then allowed to gradually cool to room temperature. The mixture was then further cooled to 0 to 3° C. in an ice bath and stirred at that temperature for 1 h. The resulting slurry was filtered and the filter cake was washed with chilled 2-propanol (3×35 mL) and dried under reduced pressure at 60° C. to leave a white solid (29.949 g).

Method 3

Preparation of
2-Chloro-N-(4-chlorophenethyl)propan-1-amine
(Compound VI) Hydrochloride Into a 250 mL round bottom flask equipped with overhead stirring, a thermocouple, a condenser, and a nitrogen bubbler vented to a caustic scrubber, was charged 1-(4-chlorophenethylamino)propan-2-ol (Compound V) (8.000 g, 37.4 mmol). Toluene (40 mL, 376 mmol) was added and the mixture was heated in oil bath at 55° C. Dissolution occurred at an internal temperature of about 40° C. N,N-Dimethylacetamide (1.052 mL, 11.23 mmol) was added. Then thionyl chloride (3.47 mL, 47.5 mmol) was added at an initial internal temperature of 50° C. and at a rate sufficient to maintain the internal temperature at <65° C. The mixture became cloudy. On completion of the addition, the temperature of the bath was raised to 68° C. A dark brown solution formed which gradually thickened into a beige slurry. Stirring was continued at between 60° C. and 65° C. for 2.5 h. Isopropanol (6.84 mL, 89 mmol) was added and the mixture was heated to a gentle reflux at (83° C. internal temperature). Stirring was continued at gentle reflux for 2 h and then heating was discontinued. The reaction was allowed to gradually cool to room temperature overnight. Next, the mixture was cooled in an ice bath to an internal temperature of <2° C. over about 45 min and stirring was continued at between 0° C. and 2° C. for 2 h. The resulting slurry was filtered through a Whatman™ funnel under reduced pressure, washing with isopropanol (2×15 mL). The cake was dried under reduced pressure at room temperature to leave the title compound as a light-beige solid (9.278 g).

For the ultraviolet spectrum of Compound (VI) prepared by Method 3 see FIG. 1.

Method 4

Step A: Preparation of
1-Chloro-4-(2-chloroethyl)benzene (Compound III)

A 10-liter jacketed reactor equipped with an overhead stirrer, a thermocouple, an addition funnel, and a dry ice/acetone condenser was charged with 2-(4-chlorophenyl)ethanol (2005 g, 12.8 mol) and swept with nitrogen. DMF (49.6 mL, 640 mmol) was charged to the reactor and the reactor contents were heated to 60° C. Thionyl chloride (1607.3 g) was added at a rate sufficient to maintain the temperature at >49° C. and <70° C. On completion of the addition, the reaction was held at 52.6° C. (jacket temperature). It was then cooled to 20° C. and allowed to stir at room temperature overnight. The reaction mixture was concentrated at 22 torr and 60° C. (water bath) for 1.5 h, to leave 1-chloro-4-(2-chloroethyl)benzene (2256 g).

Step B: Preparation of
1-(4-Chlorophenethylamino)propan-2-ol (Compound V)

Into a 250-mL round-bottom flask equipped with a magnetic stir bar, a thermocouple, a condenser, and a nitrogen bubbler, was charged 1-amino-2-propanol (54.1 g, 720 mmol). The reactor contents were heated in an oil bath to an internal temperature of 85° C. 1-Chloro-4-(2-chloroethyl) benzene (25.218 g, 144 mmol) was slowly charged via addition funnel, while maintaining the internal temperature at <100° C. On completion of the addition, stirring was continued at an internal temperature between 90° C. and 95° C. for 3 h. The reaction was allowed to cool to 40° C. (bath) and stirring was continued at that temperature overnight. Chlorobenzene (50 mL) was charged to the flask followed by water (25 mL) and the mixture was stirred at 80° C. (bath) for 15 min. The layers were then allowed to separate at room temperature and the organic phase was removed. The aqueous phase was extracted with chlorobenzene (2×25 mL) at 80° C. (bath). The organic phases were combined and washed with water (25 mL) at 80° C. (bath). The organic phase was removed and concentrated at 60° C. (water bath) under reduced pressure. A total of 69.261 g of distillate was removed by distillation. The residue was diluted with chlorobenzene (62.4 mL). The resulting mixture, which contained 0.0172% water by Karl Fischer titration, was carried forward to Step C without further purification.

Step C: Preparation of
2-Chloro-N-(4-chlorophenethyl)propan-1-amine
(Compound VI) Hydrochloride The chlorobenzene solution of 1-(4-chlorophenethylamino)propan-2-ol from Step B was transferred with more chlorobenzene (25 mL) to a 500-mL round-bottom flask equipped with overhead stirring, a thermocouple, a condenser, and a nitrogen bubbler vented to a caustic scrubber. The mixture was heated in an oil bath to 50° C. (internal temperature) and thionyl chloride (15.72 mL, 216 mmol) was added slowly over about 50 min while maintaining at the internal temperature at <65° C. The solution became a white slurry and then a light brown slurry, easily stirring. On completion of the addition, a dark brown solution was obtained, which was heated to 60° C. (internal temperature). After about 3 min at that temperature a milky, light-brown mixture formed and stirring was continued at between 60° C. and 65° C. for 4 h, during which time the mixture thickened, and became a golden/orange/beige color. Isopropanol (26.0 ml, 340 mmol) was added and an easily stirrable slurry formed. This was heated to gentle reflux, stirred for 2 h at between 79° C. and 82° C. (internal temperature) and then allowed to gradually cool to room temperature and stirred overnight. The reaction was next cooled to <2° C. over about 45 min and stirred at between 0° C. and 2° C. for 2 h. The resulting slurry was filtered through a Whatman™ funnel under reduced pressure, washing with chilled isopropanol (3×25 mL). The cake was dried on the filter at room temperature for 1.5 h to afford an off-white solid (32.084 g). For the ultraviolet spectrum of this crude product see FIG. 2.

Figure 2:
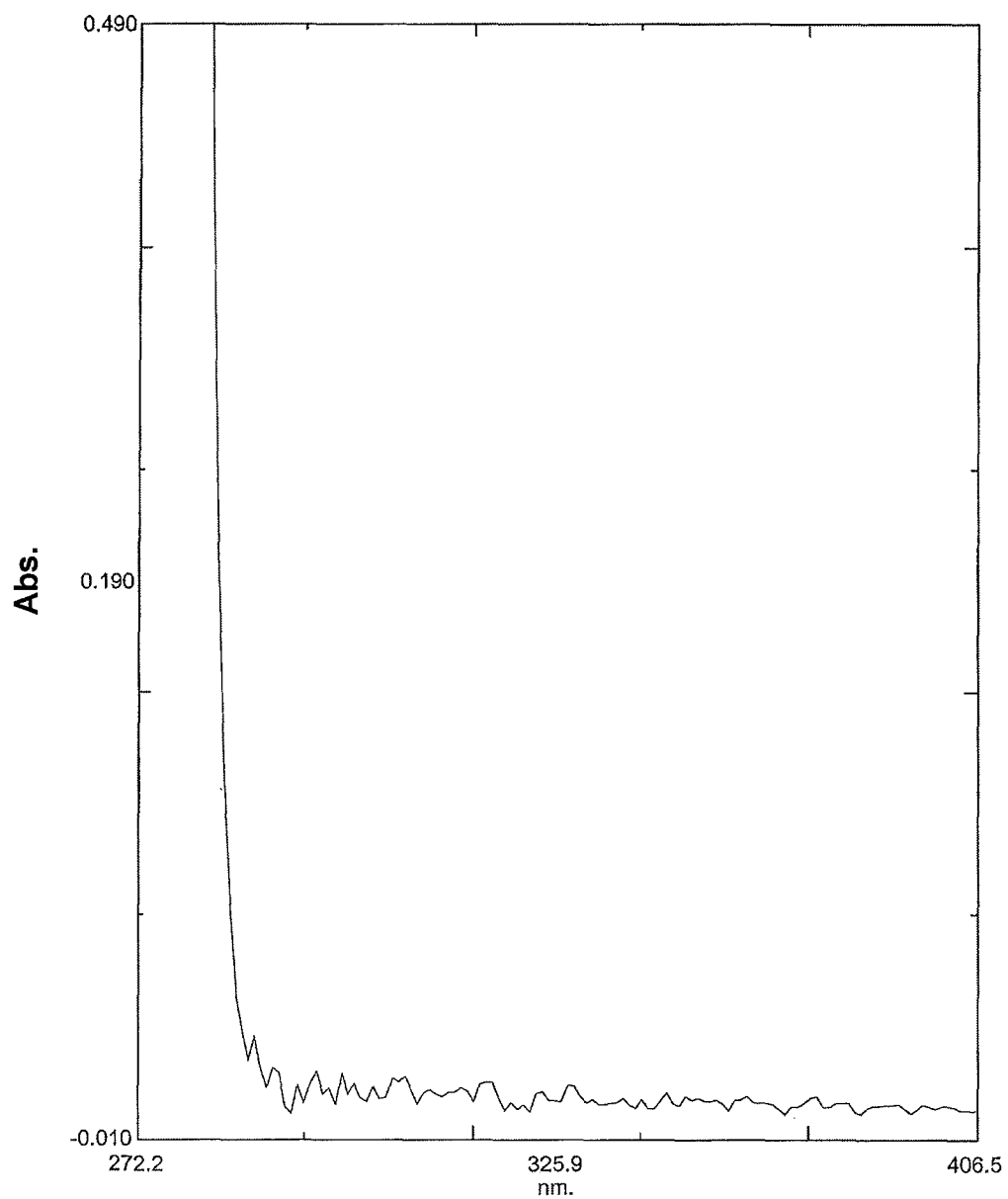
FIG. 2 shows the ultraviolet spectrum of 2-chloro-N-(4-chlorophenethyl)propan-1-amine (Compound VI) hydrochloride prepared according to the procedure described in Example 1, Method 4.

A comparison of FIGS. 1 and 2 show that when the chlorination of 1-(4-chlorophenethylamino)propan-2-ol (Compound V) is performed in chlorobenzene (Method 4) rather than toluene/DMA (Method 3) the UV purity profile of the resulting 2-chloro-N-(4-chlorophenethyl)propan-1-amine (Compound VI) hydrochloride is improved.

A portion of the solid (31.491 g) was transferred to a 500-mL round-bottom flask equipped with overhead stirring, a thermocouple, a condenser, and a nitrogen bubbler. Isopropanol (85 mL) was added and the mixture was heated to a gentle reflux. Concentrated HCl (0.432 ml, 5.19 mmol) was added to the slurry during heating to give a pH of 1-2 by pH paper. Stirring at 80 to 83° C. was continued for a further 75 min and then water (11.5 mL) was charged forming a solution. The solution was gradually cooled to room temperature and precipitation began at between 70° C. and 74° C. (internal temperature). Once at room temperature, the mixture was cooled further in an ice bath to <2° C. and stirring was continued at between 0° C. and 2° C. for 1 h. The resulting white slurry was filtered through a Whatman™ funnel under reduced pressure, washing with chilled isopropanol (2×25 mL). The solid was dried on the filter at room temperature and then at 60° C. under reduced pressure overnight to leave the title compound (28.286 g, 105 mmol, 73.1%) as a white solid (HPLC assay=101.7%).

Method 5

Step A: Preparation of 1-(4-Chlorophenethylamino)propan-2-ol (Compound V)

Into a 5-L jacketed reactor equipped with a chiller, overhead stirring, an anchor impeller, a thermocouple, a glycol condenser, and a nitrogen inlet vented to a caustic scrubber, was charged 1-aminopropan-2-ol (1102 mL, 14.3 mol). The reactor contents were heated to 80° C. whilst stirring at 250 rpm under a nitrogen sweep. 1-Chloro-4-(2-chloroethyl)benzene (Method 4, Step A, 500 g, 2856 mmol) was charged dropwise via an addition funnel over 1 h to give a clear golden oil. During the addition significant off-gassing was observed and the internal temperature reached 93° C. The reaction was stirred for a further 2 h at 90 to 95° C. Water (500 mL) and chlorobenzene (1000 mL) were added. The internal temperature dropped to 74° C. during the addition. The mixture was stirred at 70 to 75° C. for 15 min and then the layers were allowed to separate. The lower organic product phase was removed, and the upper aqueous phase was extracted with chlorobenzene (2×500 mL) by stirring at 70 to 75° C. for 15 min. The combined organic phases were washed with water (2×500 mL) by stirring at 70 to 75° C. for 15 min. After removal of the aqueous, the chlorobenzene solution containing the title compound was stirred overnight under nitrogen at 50° C. (jacket). Next, the solvent was removed by distillation under reduced pressure and the residue was diluted with chlorobenzene (2500 mL). The resulting solution contained 0.03% water by Karl-Fischer titration.

Step B: Preparation of 2-Chloro-N-(4-chlorophenethyl)propan-1-amine (Compound VI) Hydrochloride The solution of 1-(4-chlorophenethylamino)propan-2-ol prepared in Step B was cooled to 50° C., and via addition funnel thionyl chloride (313 mL, 4284 mmol) was charged dropwise over 55 min. Initially, the solution became yellow, off-gassing was observed and the internal temperature increased to 56° C. The jacket temperature was decreased to 45° C. and as the addition continued the mixture became a light brown slurry then a dark brown solution during which time the internal temperature reached 64° C. Upon completion of the addition, the reaction was stirred at between 60 and 65° C. for 4 h to give a thick, light-brown slurry. Next, isopropanol (519 mL) was charged resulting in a slight exotherm to 67° C. and significant off-gassing. The mixture was heated to reflux and stirred for 2 h, then cooled to between 0 and 1° C. and stirred overnight. The resulting slurry was filtered through a medium fritted 3-L glass funnel under reduced pressure and the reactor was washed forward with cooled isopropanol (2×500 mL). The cake (724 g) was transferred to a drying tray and dried at 60° C. under reduced pressure over 3 days to give the title compound as a very light beige solid (617 g, 80%) (99.47 area % by HPLC; UV: $\lambda_{max}$ 333 nm, 0.045 AU).

Method 6

Step A: Preparation of 1-Chloro-4-(2-chloroethyl)benzene (Compound III)

Into a 250-mL round-bottom flask equipped with magnetic stirring, a thermocouple, a condenser, and a nitrogen bubbler vented to a caustic scrubber, was charged 2-(4-chlorophenyl) ethanol (25.026 g, 160 mmol) N,N-dimethylformamide (0.621 mL, 7.99 mmol) was added and the mixture was heated to 58° C. Thionyl Chloride (12.25 mL, 168 mmol) was charged over 1 h while the temperature was maintained at <65° C. Upon completion of the addition, the mixture was stirred at 60 to 64° C. for 2.5 h, and then allowed to gradually cool to room temperature and stirred overnight to give a clear, golden oil.

Step B: Preparation of 1-(4-Chlorophenethylamino)propan-2-ol (Compound V)

Into a 250-mL round-bottom flask equipped with a magnetic stir bar, a thermocouple, a condenser, and a nitrogen bubbler vented to a caustic scrubber, was charged 1-aminopropan-2-ol (60.0 g, 799 mmol). The mixture was heated to 85° C. and the product from Step A was added while maintaining the reaction temperature below 98° C. Upon completion of the addition the reaction mixture was stirred at 90 to 95° C. for 2.5 h. Chlorobenzene (50 mL) and water (25 mL) were added and the mixture was stirred at 70 to 75° C. for 15 min. The phases were allowed to separate and the lower organic phase was removed. The upper aqueous phase was extracted with chlorobenzene (2×25 mL) at 70 to 75° C. The combined organic phases were washed with water (2×25 mL) at 70 and 75° C. and 87.5 g of solvent was removed by distillation under reduced pressure at 60° C. (bath). The residue was diluted with chlorobenzene (125 mL). The resulting orange solution, which contained 0.032% water by Karl Fischer titration, was stirred overnight at 45° C. (bath).

Step C: Preparation of 2-Chloro-N-(4-chlorophenethyl)propan-1-amine (Compound VI) Hydrochloride The solution of 1-(4-chlorophenethylamino)propan-2-ol prepared in Step B was heated to 50° C. and thionyl Chloride (17.50 mL, 240 mmol) was charged over 50 min while the internal temperature was maintained at <69° C. The reaction mixture became a dark-brown solution during the addition. The reaction was then stirred at 60 to 65° C. for 3 h to form a brown slurry. Isopropanol (25 mL) was added portionwise and the mixture was heated to reflux and stirred for 1 h. The mixture was allowed to gradually cool to room temperature and then stirred at 0 to 2° C. for 1 h. The resulting slurry was filtered under reduced pressure, and the cake was washed with isopropanol (2×25 mL) and dried at 60° C. under reduced pressure overnight to give the title compound as an off-white solid (31.743 g, 74.0%) (99.48 area % by HPLC; UV: $\lambda_{max}$ 322 nm, 0.045 AU, 40 mg/mL MeOH).

Method 7

Step A: Preparation of 1-Chloro-4-(2-chloroethyl)benzene (Compound III)

Into a 250-mL round-bottom flask equipped with magnetic stirring, a thermocouple, a condenser, and a nitrogen bubbler vented to a caustic scrubber, was charged 2-(4-chlorophenyl) ethanol (25.033 g, 160 mmol). N,N-Dimethylacetamide (0.749 mL, 7.99 mmol) was added and the mixture was heated in oil bath to 58° C. Thionyl Chloride (12.25 mL, 168 mmol) was charged over 1 h while the reaction temperature was maintained at <66° C. The resulting brown solution was stirred at 60 to 64° C. for 2.5 h and then allowed to gradually cool to room temperature leaving a dark brown oil.

Step B: Preparation of 1-(4-Chlorophenethylamino)propan-2-ol (Compound V)

The title compound was prepared according to the method described in Method 6, Step B and used without further purification.

Step C: Preparation of 2-Chloro-N-(4-chlorophenethyl)propan-1-amine (Compound VI) Hydrochloride The title compound was prepared according to the method described in Method 6, Step C to give an off-white/beige solid (32.480 g, 76%) (99.52 area % by HPLC; UV: $\lambda_{max}$ 323 nm, 0.102 AU, 40 mg/mL MeOH).

A comparison of Methods 6 and 7 show that the UV purity profile of 2-chloro-N-(4-chlorophenethyl)propan-1-amine (Compound VI) hydrochloride is improved if DMF rather than DMA is used in Step A.

Method 8

Step A: Preparation of 1-Chloro-4-(2-chloroethyl)benzene (Compound III)

Into a 250-mL round-bottom flask equipped with magnetic stirring, a thermocouple, a condenser, and a nitrogen bubbler vented to caustic scrubber, was charged 2-(4-chlorophenyl) ethanol (25.119 g, 160 mmol), toluene (73 mL) and N,N-dimethylacetamide (0.751 ml, 8.02 mmol). The mixture was heated in oil bath to between 65 and 70° C. and thionyl chloride (12.29 ml, 168 mmol) was charged over 1 h with a maximum reaction temperature of 69° C. The reaction was then stirred for 2 h at 65 to 70° C. The resulting dark-brown solution was cooled to 40° C. and washed with water (2×40 mL) by stirring for 2-5 min at 45° C. (bath) and separating the phases at room temperature. The organic phase was further washed with saturated aqueous sodium bicarbonate solution (3×40 mL) by stirring for 2-5 min at 50° C. (bath) and separating the phases at room temperature.

Step B: Preparation of 1-(4-Chlorophenethylamino)propan-2-ol (Compound V)

In a 500-mL round-bottom flask equipped with magnetic stirring, a thermocouple, a condenser, and a nitrogen bubbler vented to a caustic scrubber, 1-aminopropan-2-ol (60.2 g, 802 mmol) was heated to 120° C. The solution of 1-chloro-4-(2-chloroethyl)benzene in toluene prepared in Step A was added dropwise over 70 min at 114° C. to 120° C. and upon completion of the addition, the mixture was stirred at reflux for a further 2 h and then allowed to cool to 72° C. Aqueous NaOH (50%, 12.83 g, 160 mmol) and water (25 mL) were added and the mixture was stirred at 70 to 73° C. for approximately 5 minutes. The phases were allowed to separate, the aqueous phase was removed, and the organic phase washed at 80° C. (bath) for approximately 5 min with water (4×25 mL). The combined aqueous phases were extracted with toluene (37 mL) at 80° C. (bath). The combined organic phases were concentrated under reduced pressure at 60° C. (bath) and then at room temperature overnight to leave the title compound as a white solid.

Step C: Preparation of 2-Chloro-N-(4-chlorophenethyl)propan-1-amine (Compound VI) Hydrochloride In a 500-mL round-bottom flask equipped with overhead stirring, a thermocouple, a condenser, and a nitrogen bubbler vented to a caustic scrubber, was charged thionyl chloride (12.29 ml, 168 mmol) and toluene (30 mL) and the mixture was heated to 75° C. (bath). To this was added over 1 h a solution of the 1-(4-chlorophenethylamino)propan-2-ol prepared in Step B in toluene (80 mL) at 50° C. The resulting easily-stirred, dark-beige slurry was stirred at 70 to 75° C. for 2.5 h. Isopropanol (17 mL) was added and the mixture was heated to reflux, stirred for 1 h and then allowed to gradually cool to room temperature. The resulting slurry was filtered under reduced pressure and the solid was washed with isopropanol (~150 mL) and dried under reduced pressure overnight. The crude product was suspended in a mixture of isopropanol (113 mL) and water (12 mL) in a flask equipped with overhead stirring, a thermocouple, a condenser, and a nitrogen bubbler vented to a caustic scrubber. HCl (0.474 mL, 5.77 mmol) was added and the mixture was heated to 80° C. by which point the solid had dissolved. The mixture was next allowed to gradually cool to room temperature with precipitation commencing near 73° C. The slurry was filtered under reduced pressure and the solid was washed with isopropanol (~70 mL). The solid was dried at 60° C. under reduced pressure to leave the title compound as a white solid (32.211 g, 74.8%) (100 area % by HPLC).

Method 9

Step A: Preparation of 1-Chloro-4-(2-chloroethyl)benzene (Compound III)

Into a 250-mL round-bottom flask equipped with magnetic stirring, a thermocouple, a condenser, and a nitrogen bubbler vented to caustic scrubber, was charged 2-(4-chlorophenyl) ethanol (25.011 g, 160 mmol), N,N-dimethylacetamide (0.748 mL, 7.99 mmol), and toluene (73 mL). The mixture was heated to 65 to 70° C. and then thionyl chloride (12.24 mL, 168 mmol) was added over 1 h. The reaction was stirred at 60 to 68° C. for 2 h to give a dark-brown solution. This solution was cooled to 45° C., washed with water (2×27 mL) and saturated aqueous sodium bicarbonate (3×27 mL) at 40 to 45° C., and then cooled room temperature and allowed to stir overnight.

Step B: Preparation of 1-(4-Chlorophenethylamino)propan-2-ol (Compound V)

1-Aminopropan-2-ol (60.0 g, 799 mmol) was charged to a 250-mL round-bottom flask equipped with a magnetic stir bar, a thermocouple, a condenser, and a nitrogen bubbler vented to a caustic scrubber, and heated to 120° C. To this was slowly added the toluene solution of 1-chloro-4-(2-chloroethyl)benzene from Step A while maintaining the reaction temperature at 120-125° C. On completion of the addition, stirring was continued at 115-120° C. for 2.5 h. NaOH (50%, 12.78 g, 160 mmol) was added followed by water (25 mL) and the mixture was stirred at 70 to 75° C. for 15 min. The organic phase was separated and washed with water (4×25 mL) at 70 to 75° C. The combined aqueous phases were extracted with toluene (38 mL) for 15 min at 70 to 75° C. Then, the combined organic phases were concentrated under reduced pressure at 60° C. (bath). The residue was diluted with toluene to a total volume of 104 mL and the golden solution was stirred overnight at 50° C. (bath) under nitrogen. Karl Fischer titration showed 0.052% water.

Step C: Preparation of
2-Chloro-N-(4-chlorophenethyl)propan-1-amine
(Compound VI) Hydrochloride A 500-mL round-bottom flask equipped with overhead stirring, a thermocouple, a condenser, and a nitrogen bubbler vented to a caustic scrubber, was charged toluene (30 mL) followed and thionyl chloride (12.24 mL, 168 mmol) and the solution was heated to 75° C. (bath). In a separate flask, the toluene solution of 1-(4-chlorophenethylamino)propan-2-ol from Step B was heated to 55° C. (bath) and then added to the thionyl chloride solution portionwise over 75 min with a maximum reaction temperature of 72° C. On completion of the addition, the resulting thick, beige slurry was stirred at 70 to 75° C. for 2.5 h. Isopropanol (17 mL) was added and the mixture was heated to reflux, stirred for 1 h, and then allowed to gradually cool to room temperature. The beige slurry was filtered and the solid was washed with isopropanol (53 mL) in two portions. The cake was dried at 60° C. under reduced pressure overnight to leave the title compound as an off-white solid (34.458 g, 80%) (99.14 area % by HPLC; UV: $\lambda_{max}$ 321 nm, 0.057 AU, 40 mg/mL MeOH).

Method 10

Step A: Preparation of
1-Chloro-4-(2-chloroethyl)benzene (Compound III)

Into a 250-mL round-bottom flask equipped with magnetic stirring, a thermocouple, a condenser, and a nitrogen bubbler vented to caustic scrubber, was charged 2-(4-chlorophenyli-ethanol (25.058 g, 160 mmol) and N,N-dimethylformamide (0.622 mL, 8.00 mmol). The mixture was heated to 58° C. and thionyl chloride (12.26 mL, 168 mmol) was added over 1 h at <65° C. Stirring was continued at 60 to 63° C. for 2 h to give a golden yellow oil, which was allowed to gradually cool to room temperature and stirred overnight.

Step B: Preparation of
1-(4-Chlorophenethylamino)propan-2-ol (Compound V)

In a separate 250-mL round-bottom flask equipped with a magnetic stir bar, a thermocouple, a condenser, and a nitrogen bubbler vented to a caustic scrubber, was charged 1-aminopropan-2-ol (60.1 g, 800 mmol), which was then heated to 85° C. To this was slowly added the toluene solution of 1-chloro-4-(2-chloroethyl)benzene from Step A while maintaining the reaction temperature at <99° C. On completion of the addition, stirring was continued at 90 to 95° C. for 2 h. Toluene (50 mL) and water (25 mL) were added and the mixture was stirred at 70 to 75° C. for 15 minutes before the phases were separated at room temperature. The upper aqueous phase was extracted with toluene (2×25 mL) at 70 to 75° C. Then, the combined organic phases were washed with water (2×25 mL) at 70 to 75° C., and concentrated by distillation under reduced pressure at 60° C. (bath). The residue was diluted with toluene to a total volume of 112.5 mL and the yellow solution was stirred under nitrogen overnight at 50° C. (bath). Karl Fischer titration showed 0.091% water.

Step C: Preparation of
2-Chloro-N-(4-chlorophenethyl)propan-1-amine
(Compound VI) Hydrochloride A 500-mL round-bottom flask equipped with overhead stirring, a thermocouple, a condenser, and a nitrogen bubbler vented to a caustic scrubber, was charged toluene (30 mL) followed and thionyl chloride (12.26 mL, 168 mmol) and the solution was heated to 75° C. (bath). In a separate flask, the toluene solution of 1-(4-chlorophenethylamino)propan-2-ol from Step B was heated to 55° C. (bath) and then added to the thionyl chloride solution portionwise over 75 min with a maximum reaction temperature of 74° C. On completion of the addition, the resulting thick, beige slurry was stirred at 70 to 75° C. for 2.5 h. Isopropanol (17 mL) was added and the mixture was heated to reflux, stirred for 1 h, and then allowed to gradually cool to room temperature. The beige slurry was filtered and the solid was washed with isopropanol (53 mL) in two portions. The cake was dried at 60° C. under reduced pressure overnight to leave the title compound as an off-white solid (32.410 g, 75%) (99.57 area % by HPLC; UV: $\lambda_{max}$ 321 nm, 0.054 AU, 40 mg/mL MeOH).

Method 11

Step A: Preparation of
1-Chloro-4-(2-chloroethyl)benzene (Compound III)

Into a 250-mL round-bottom flask equipped with magnetic stirring, a thermocouple, a condenser, and a nitrogen bubbler vented to caustic scrubber, was charged 2-(4-chlorophenyl) ethanol (25.145 g, 161 mmol) and N,N-dimethylacetamide (0.752 mL, 8.03 mmol). The mixture was heated to 55 to 60° C. and then thionyl chloride (12.30 mL, 169 mmol) was added over 1 h at <62° C. The reaction mixture was stirred at 58 to 62° C. for 2 h and then allowed to cool to <30° C. to give the title compound as a dark brown solution (29.730 g) containing N,N-dimethylacetamide and thionyl chloride. This was transferred to an addition funnel using toluene (5 mL).

Step B: Preparation of
1-(4-Chlorophenethylamino)propan-2-ol (Compound V)

In a 500-mL round-bottom flask equipped with magnetic stirring, a thermocouple, a condenser, and a nitrogen bubbler vented to caustic scrubber, was charged 1-aminopropan-2-ol (60.3 g, 803 mmol), which was then heated to 85° C. To this was slowly added the product from Step A over 1 hour with a maximum reaction temperature of 98° C. The addition funnel was washed forward with toluene (5 mL). The resulting golden solution was stirred at 90 to 95° C. for 2 h. Toluene (51 mL) and water (25 mL) were added and the mixture was stirred for 15 min at 75 to 80° C. before the layers were allowed to separate at room temperature. The lower aqueous phase was extracted with toluene (2×25 mL) at 70 to 75° C.

The combined toluene phases were washed with water (2×25 mL) at 70 to 75° C. and then concentrated under reduced pressure first at 60° C. (bath) and then at room temperature overnight to leave an off-white/yellowish solid. The solid was dissolved in toluene (80 mL) at 55° C. (bath) to give a solution which contained 0.0170% water by Karl Fischer titration.

Step C: Preparation of 2-Chloro-N-(4-chlorophenethyl)propan-1-amine (Compound VI) Hydrochloride A 500-mL flask equipped with overhead stirring, a thermocouple, a condenser, and a nitrogen bubbler vented to a caustic scrubber, was charged with toluene (30 mL) followed by thionyl chloride (12.30 mL, 169 mmol) and the solution was heated to 75° C. (bath). In a separate flask, the toluene solution of 1-(4-chlorophenethylamino)propan-2-ol from Step B was heated to 55° C. (bath) and then added to the thionyl chloride solution portionwise over 75 min with a maximum reaction temperature of 73° C. On completion of the addition, the resulting thick, beige slurry was stirred at 72 to 76° C. for 3 h. Isopropanol (17 mL) was added and the mixture was heated to reflux, stirred for 1 h, and then allowed to gradually cool to room temperature. The beige slurry was filtered and the solid was washed with isopropanol (54 mL) in three portions. The cake was dried overnight at room temperature to leave an off-white solid (33.959 g, 79%). The crude product was suspended in isopropanol (113 mL) and water (12 mL) in a 500-mL round-bottom flask equipped with overhead stirring, a thermocouple, a condenser, and a nitrogen bubbler vented to a caustic scrubber. HCl (0.600 mL, 7.31 mmol) was added and the mixture was heated to 81° C. to form a solution. The solution was allowed to gradually cool to room temperature and the product began to crystallize at between 65 and 70° C. The resulting slurry was cooled further to 0 to 2° C. (ice bath) and then filtered under reduced pressure. The solid was washed with isopropanol (54 mL) in 3 portions and then dried under reduced pressure first at room temperature and then at 60° C. overnight to give the title compound as a white solid (31.607 g, 73.3%) (100 area % by HPLC).

Method 12

Step A: Preparation of 1-Chloro-4-(2-chloroethyl)benzene (Compound III)

In a 250-mL round bottom flask equipped with overhead stirring, a thermocouple, a condenser, and a nitrogen bubbler vented to a caustic scrubber, 2-(4-chlorophenyl)ethanol (40.011 g, 255 mmol) and N,N-dimethylacetamide (1.197 mL, 12.77 mmol) were heated to 55° C. Thionyl chloride (19.58 mL, 268 mmol) was added slowly and significant off-gassing was observed. After the addition was complete the resulting dark-brown solution was stirred at between 60 and 64° C. for 1.5 hours and then allowed to cool to room temperature and stirred overnight to give the title compound as a dark-brown oil (47.060 g, including DMA and thionyl chloride).

Step B: Preparation of 1-(4-Chlorophenethylamino)propan-2-ol (Compound V)

In a 500-mL round-bottom flask equipped with a magnetic stir bar, a thermocouple, a condenser, and a nitrogen bubbler vented to a caustic scrubber, was charged 1-aminopropan-2-ol (96 g, 1277 mmol). This was heated in oil bath at 90° C. and the solution of chloro-4-(2-chloroethyl)benzene from Step A was slowly added over 1.25 h at a maximum temperature of 95° C. The reaction was stirred at 90 to 95° C. for 2 h and then toluene (80 mL) and water (40 mL) were added. The mixture was stirred for 15 min at 70 to 80° C. and then the phases were allowed to separate at room temperature. The aqueous phase was extracted with toluene (2×40 mL). The combined toluene phases were washed with water (2×40 mL) at 70 to 80° C. and then concentrated under reduced pressure at 60° C. Toluene was added to the residue to give a total volume of 170 mL and the solution was stirred overnight at 55° C. (bath). This solution was found to contain 0.052% water by Karl Fischer titration.

Step C: Preparation of 2-Chloro-N-(4-chlorophenethyl)propan-1-amine (Compound VI) Hydrochloride Into a 500-mL round-bottom flask equipped with overhead stirring, a thermocouple, a condenser, and a nitrogen bubbler vented to a caustic scrubber, was charged thionyl chloride (9.79 mL, 134 mmol) in toluene (24 mL). The mixture was heated to 75° C. and one half of the toluene solution of 1-(4-chlorophenethylamino)propan-2-ol from Step B (at 55° C.) was added over 1 h to form a light-brown slurry. The maximum temperature during the addition was 75° C. The slurry was then stirred at 70 to 75° C. for 2.25 h. Isopropanol (84 mL) was added and the mixture was heated to reflux for 1 h and then allowed to gradually cool to room temperature overnight. The resulting slurry was filtered under reduced pressure and the solid was washed isopropanol (3×14.2 mL, then 21.3 mL, and then 42.6 mL). The round-bottom flask was rinsed with further isopropanol (3×14.2 mL, then 21.4 mL, and then 21.2 mL) and the rinsings were used to wash the filter cake. The cake was then dried under reduced pressure at 60° C. overnight. The title compound was isolated with a purity of 99.79 area % by HPLC; UV: $\lambda_{max}$ 320 nm, 0.12 AU, 40 mg/mL MeOH).

Method 13

Step A: Preparation of 1-(4-Chlorophenethylamino)propan-2-ol (Compound V)

Into a 1-L jacketed reactor equipped with a retreat curve stir blade, overhead stirring, a thermocouple, a condenser, and a nitrogen bubbler was charged 1-aminopropan-2-ol (110 mL, 1430 mmol), which was then heated to 85 and 90° C. 1-Chloro-4-(2-chloroethyl)benzene (50.054 g, 286 mmol) was charged via addition funnel over 1 h with a maximum reaction temperature of 93° C. Stirring was then continued at 90 to 95° C. for 2.5 h. Chlorobenzene (100 mL) and water (50 mL) were added and the mixture was stirred at 70 to 75° C. for 15 min. The phases were allowed to separate and the aqueous phase was extracted with chlorobenzene (2×50 mL) at 70 to 75° C. The combined organic phases were then washed with water (2×50 mL) at 70 to 75° C. and concentrated by distillation under reduced pressure. The residue was dissolved in chlorobenzene to a total weight of 503 g and allowed to stand at room temperature overnight. A solid precipitate formed which was redissolved by adding chlorobenzene (50 mL) and heating the mixture at 30 to 35° C.

Step B: Preparation of 2-Chloro-N-(4-chlorophenethyl)propan-1-amine (Compound VI) Hydrochloride The solution of 1-(4-chlorophenethylamino)propan-2-ol in chlorobenzene from Step A at room temperature was added dropwise over 1 h to a stirred solution of thionyl chloride (31.3 mL, 429 mmol) in chlorobenzene (50 mL) at 58 to 66° C. The resulting golden slurry was stirred at 60 to 65° C. for 5 h and then at gentle reflux for 1 h. The reaction was allowed to gradually cool to room temperature overnight and then cooled to 0 to 3° C. over 1 h. Stirring was continued at 0 to 3° C. for 1 h and then the product was isolated by filtration through a medium-fitted glass funnel. The solid was washed with isopropanol (2×50 mL) and dried at 60° C. under reduced pressure to leave the title compound as an off-white solid (57.687 g, 75%) (99.36 area % by HPLC).

Method 14

Step A: Preparation of 1-(4-Chlorophenethylamino)propan-2-ol (Compound V)

Into a 5-L jacketed reactor equipped with a chiller, overhead stirring, an anchor impeller, a thermocouple, a glycol condenser, and a nitrogen inlet vented to a caustic scrubber, was charged 1-aminopropan-2-ol (1102 mL, 14.3 mol). The reactor contents were heated to 80° C. and 1-chloro-4-(2-chloroethyl)benzene (Method 4, Step A, 500 g, 2856 mmol) was slowly charged over 40 min. The temperature of the gold-colored reaction mixture reached 97° C. during the addition and 101° C. approximately 1 min after addition was complete. The mixture was then allowed to cool to 90 to 95° C. and stirring was continued at that temperature for 2 h. Water (500 mL) and toluene (1000 mL) were added and the mixture was stirred at 75 to 80° C. for 15 min. The layers were allowed to separate at 70 to 75° C. The organic phase was removed and the aqueous phase was extracted with toluene at 70 to 75° C. for 15 min (2×500 mL). The combined organic phases were washed with water at 70 to 75° C. for 15 min (2×500 mL) and stirred overnight under nitrogen at 50° C. The solution was concentrated by distillation at 60° C. (jacket) under reduced pressure, and the residue was diluted with toluene to a total volume of about 800 mL. This solution was distilled a second time at 65° C. (jacket) under reduced pressure and the residue was diluted with toluene to a total volume of about 400 mL. The water content of the solution was 0.03% by Karl Fisher titration.

Step B: Preparation of 2-Chloro-N-(4-chlorophenethyl)propan-1-amine (Compound VI) Hydrochloride The solution of 1-(4-chlorophenethylamino)propan-2-ol prepared in Step A was cooled to 50° C. and N,N-dimethylacetamide (80 mL, 857 mmol) was added. Next, thionyl chloride (265 mL, 3627 mmol) was added dropwise with significant off-gassing observed. The internal temperature reached 70° C. and the jacket temperature was adjusted to 45° C. After 1 h the addition was complete and the resulting brown suspension was stirred at 60 to 65° C. for 3 h, Isopropanol (519 mL, 6741 mmol) was added, causing in significant off-gassing, and the mixture was heated to reflux and stirred for 2 h and then cooled to −3 to 0° C. and stirred overnight. The mixture was filtered over a medium-fritted 3-L glass funnel under reduced pressure and the solid was washed with isopropanol (2×500 mL) and dried at room temperature on the filter under reduced pressure to leave a beige wet cake (695 g). This was dried overnight at 60° C. under reduced pressure to leave a beige solid (611 g, 80%) (99.57 area % by HPLC; UV: $\lambda_{max}$ 333 nm, 0.200 AU).

A comparison of Methods 5 and 14 show that the UV purity profile of 2-chloro-N-(4-chlorophenethyl)propan-1-amine (Compound VI) hydrochloride is improved if chlorobenzene is used in Step B rather than toluene/DMA.

Method 15

Step A: Preparation of 1-(4-Chlorophenethylamino)propan-2-ol (Compound V)

A 1-L jacketed reactor was equipped with a retreat curve stir blade, overhead stirring, a thermocouple, a condenser, and a nitrogen bubbler. 1-Aminopropan-2-ol (110 mL, 1429 mmol) was added and heated to 85 and 90° C. 1-Chloro-4-(2-chloroethyl)benzene (50.032 g, 286 mmol) was added over 1 h at <97° C. and upon completion of the addition stirring was continued at 90 to 95° C. for 2.5 h. The internal temperature was reduced to 75° C. and chlorobenzene (100 mL) and water (50 mL) were added. The mixture was stirred for 15 min at 70 to 75° C. before the phases were separated. The upper aqueous phase was extracted with chlorobenzene at 70 to 75° C. (2×50 mL). The combined organic phases were washed with water at 70-75° C. (2×50 mL) and then held over the weekend at room temperature. The solution was then concentrated at 60 to 65° C. (bath) at 40 to 45 mbar to remove 143 g of distillate.

Step B: Preparation of 2-Chloro-N-(4-chlorophenethyl)propan-1-amine (Compound VI) Hydrochloride The residue from Step A was diluted with chlorobenzene to a total weight of 554 g and transferred to a 1-L jacketed reactor with further chlorobenzene (50 mL). The solution was heated to 58 to 59° C. and then thionyl chloride (31.3 mL, 429 mmol) was added over 1 h, slowly at first due to vigorous off-gassing and then more quickly towards the end of the addition. The reaction temperature reached 69° C. and the jacket temperature was lowered to 53° C. Upon completion of the addition, the internal temperature was 63° C. and some precipitation was observed. Gradually, the reaction mixture formed a slurry which was stirred at 60 to 65° C. overnight. The mixture was easily stirred during and subsequent to the addition. Isopropanol (50 mL) was added and the mixture was heated to reflux for 2 h. Next, the mixture was cooled to between 0 and 3° C. over 3 h and stirred at that temperature for 1 h. The resulting slurry was filtered through a medium-fritted glass funnel under reduced pressure. The reactor was rinsed with isopropanol (2×50 mL) with the rinsings being used to wash the cake. The cake was then dried under reduced pressure at 60° C. overnight to leave the title compound as an off-white solid (57 g, 74.2%) (99.65 area % by HPLC; UV: $\lambda_{max}$ 325 nm, 0.04 AU).

Example 2

Preparation of 8-chloro-1-methyl-2,3,4,5-tetrahydro-1H-3-benzazepine

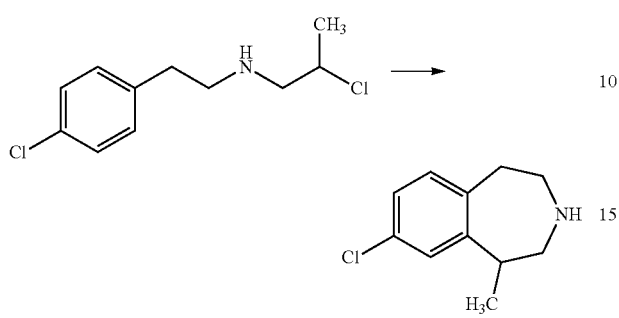

Small Scale 2-(4-Chlorophenyl)-N-ethyl-N-2-propylchloride (1 g, 4.3 mmol) was reacted with aluminum chloride (3 g, 22 mmol) in a dry 50 mL round bottom flask under nitrogen gas in an oil bath at 120° C. with stirring. Analysis by LC/MS showed complete reaction in two hours. After cooling the resulting black oil to room temperature, 20 mL ethyl acetate and 20 mL of pH 6 water were added. After 30 min of vigorous stirring the mixture was solubilized to a clear colorless upper organic layer and a brown clear lower aqueous layer. After separation of the layers, the aqueous layer was extracted two additional times with 20 mL ethyl acetate. The combined organic layers were dried over magnesium sulfate, filtered and evaporated to give 0.55 grams (55% yield) of a white to slightly yellow solid containing the HCl salt. This material was found to be very hygroscopic. The remaining aqueous layer (pH 6) was brought to pH 15 by addition of 5 grams of NaOH pellets. The aqueous layer became a thick white emulsion. Three times 40 mL of ethyl acetate were added to the thick white emulsion and decanted off. The combined organic layers were dried over magnesium sulfate, filtered and evaporated to give 0.3 g (36%) of a brown oil containing free amine. The combined yield was 91%. $^1$H NMR (CDCl$_3$): 7.2 (d, 1H, J=2.5 Hz), 7.15 (dd, 1H, J=2.5, 8 Hz), 7.05 (d, 1H, J=8 Hz), 3.6 (m, 2H), 3.5 (m, 2H), 3.1 (m, 2H), 2.9 (m, 2H), 1.5 (d, 3H, J=7 Hz). $^{13}$C NMR (CDCl$_3$): 144, 136, 133, 131, 127 (2), 51, 45, 32, 30, 17. LC/MS: 1.41 minute, 196.1 M+H$^+$ and 139 major fragment. No impurities observed.

Large Scale 2-(4-Chlorophenyl)-N-ethyl-N-2-propylchloride (49.24 g, 179.92 mmol) and aluminum trichloride (34.79 g, 260.89 mmol) were added to a flask under a nitrogen atmosphere. To this solid mixture, 1,2-dichlorobenzene (139.31 g) was added resulting in a suspension which was then heated to 120° C. which was associated with evolution of hydrogen chloride gas, which was neutralized in a sodium hydroxide filled gas scrubber. The reaction mixture became a yellow to brown solution which was heated at 120° C. for a total of 12 hours. At the end of this time HPLC analysis indicated that the ratio of product to starting material was greater than 99:1 The reaction solution was cooled to 20 to 30° C. and added dropwise to a mixture of sodium hydroxide solution (176.0 g, 1320 mmol) approx. 30%, water (79.5 g), and cyclohexane (176 g), so that the internal temperature did not exceed 50° C. The layers were separated and the lower aqueous layer was extracted with cyclohexane (74 g). The combined organic layers were extracted with a solution of aq. hydrochloric acid (22.76 g, 231 mmol) 36/38% and water (68.23 g). The organic layer was extracted with water (45.47 g). The combined aqueous layers were washed with cyclohexane (37 g). To the aqueous layer was added sodium hydroxide (40.08 g, 301 mmol) solution approx. 30% and cyclohexane (100 g). The aqueous layer was extracted with cyclohexane (100 g). The combined organic layers were concentrated at 40° C. to 60° C. and a final vacuum of 30 mbar to give 36.79 g, of a yellow oil. HPLC analysis indicated that the product had a purity of 85.45%, thus giving a corrected yield of 89.29%.

Example 3

Large Scale Preparation of L-(+)-tartaric acid salt of (R)-8-chloro-1-methyl-2,3,4,5-tetrahydro-1H-3-benzazepine Crude 8-chloro-1-methyl-2,3,4,5-tetrahydro-1H-3-benzazepine (134.32 g) was dissolved in tert-butanol (480 g). An aqueous solution of L-(+)-tartaric acid (21 g of acid in 30 g of water) and seed crystals were added. The solution was stirred at 15-25° C. overnight until crystals formed. The resulting suspension was filtered and the precipitate washed with acetone. EE was 68.1% (HPLC). The precipitate was then refluxed in additional tert-butanol (480 g) and water (10 g). Water (80 g) was added until the precipitate dissolved completely and then the solution was cooled to 15-25° C. and stirred overnight. The resulting precipitate was filtered out and washed with acetone. EE was 96.8% (HPLC). The precipiate was again refluxed in additional tert-butanol (480 g) and stirred for 1 hour at reflux. The resulting suspension was cooled to 15-25° C. and stirred overnight. The resulting precipitate was filtered out and washed with acetone. EE was 98.7% (HPLC) and the product was dried under vacuum at 60° C. Yield was 34.96 g.

Example 4

Conversion of Salt Form to Free Amine

The L-tartaric acid salt of 8-chloro-1-methyl-2,3,4,5-tetrahydro-1H-3-benzazepine (300 mg, 0.87 mmol) was added to a 25 mL round bottom flask with 50% sodium hydroxide solution (114 µL, 2.17 mmol) with an added 2 mL of water. The mixture was stirred 3 minutes at room temperature. The solution was extracted with methylene chloride (5 mL) twice. The combined organic extracts were washed with water (5 mL) and evaporated to dryness on the pump to get free amine (220 mg crude weight). LC/MS 196 (M+H).

Example 5

Preparation of Hydrochloric Acid Salt of (R)-8-chloro-1-methyl-2,3,4,5-tetrahydro-1H-3-benzazepine To a clean, dry 25 mL round bottom flask were added (R)-8-chloro-1-methyl-2,3,4,5-tetrahydro-1H-3-benzazepine free amine (220 mg), 3 mL methylene chloride, and 1.74 mL of 1M HCl in ether. The mixture was stirred for 5 minutes at room temperature. The solvent was removed under reduced pressure to give a white solid, the HCl salt. The salt was re-dissolved in methylene chloride (3 mL) and an additional 1.74 mL of 1 M HCl was added and the solution was again stirred at room temperature for 5 minutes. The solvent was removed under reduced pressure to give the desired HCl salt of 8-chloro-1-methyl-2,3,4,5-tetrahydro-1H-3-benzazapine (190 mg crude weight, 95% yield). NMR data was consistent with the desired product. $^1$H NMR (CDCl$_3$): 10.2 (br s, 1H), 9.8 (br s, 1H), 7.14 (dd, 1H, J=2, 8 Hz), 7.11 (d, 1H, J=2 Hz), 7.03 (d, 1H, J=8 Hz), 3.6 (m, 2H), 3.5 (m, 2H), 2.8-3.0 (m, 3H), 1.5 (d, 3H, J=7 Hz).

Those skilled in the art will recognize that various modifications, additions, substitutions, and variations to the illustrative examples set forth herein can be made without departing from the spirit of the invention and are, therefore, considered within the scope of the invention.

What is claimed is:

1. A process for preparing a compound selected from: 2-chloro-N-(4-chlorophenethyl)propan-1-amine (Compound VI), which has the following structure:

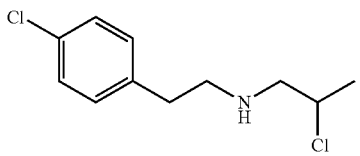

VI and salts thereof; comprising the following steps:
(a) reacting 2-(4-chlorophenyl)ethanol (Compound II):

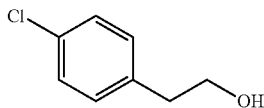

II or a salt thereof, with a first chlorinating agent to form 1-chloro-4-(2-chloroethyl)benzene (Compound III):

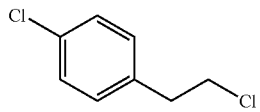

III wherein
said reacting 2-(4-chlorophenyl)ethanol or a salt thereof, with said first chlorinating agent, is performed in the presence of a first catalyst, wherein said first catalyst comprises N,N-dimethylformamide, and
the molar ratio of said 2-(4-chlorophenyl)ethanol or a salt thereof and said first catalyst is about 25:1 to about 5:1;
(b) reacting said 1-chloro-4-(2-chloroethyl)benzene (Compound III) with 1-aminopropan-2-ol (Compound IV):

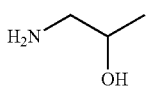

IV or a salt thereof, to form 1-(4-chlorophenethylamino)propan-2-ol (Compound V):

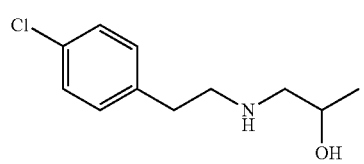

V or a salt thereof; and
(c) reacting said 1-(4-chlorophenethylamino)propan-2-ol (Compound V) or a salt thereof, with a second chlorinating agent to form said compound selected from: 2-chloro-N-(4-chlorophenethyl)propan-1-amine (Compound VI) and salts thereof; wherein
said reacting 1-(4-chlorophenethylamino)propan-2-ol or a salt thereof, with said second chlorinating agent, is performed in the presence of a first halogenated solvent, wherein said first halogenated solvent comprises chlorobenzene.

2. The process according to claim 1 wherein said first chlorinating agent comprises thionyl chloride.

3. The process according to claim 1, wherein said reacting 2-(4-chlorophenyl)ethanol or a salt thereof, with said first chlorinating agent, is performed in a reaction mixture which comprises less than 5% solvent by volume.

4. The process according to claim 3, wherein said reacting 2-(4-chlorophenyl)ethanol or a salt thereof, with said first chlorinating agent, is performed in a reaction mixture which comprises less than 4% solvent by volume.

5. The process according to claim 4, wherein said reacting 2-(4-chlorophenyl)ethanol or a salt thereof, with said first chlorinating agent, is performed in a reaction mixture which comprises less than 3% solvent by volume.

6. The process according to claim 5, wherein said reacting 2-(4-chlorophenyl)ethanol or a salt thereof, with said first chlorinating agent, is performed in a reaction mixture which comprises less than 2% solvent by volume.

7. The process according to claim 6, wherein said reacting 2-(4-chlorophenyl)ethanol or a salt thereof, with said first chlorinating agent, is performed in a reaction mixture which comprises less than 1% solvent by volume.

8. The process according to claim 7, wherein said reacting 2-(4-chlorophenyl)ethanol or a salt thereof, with said first chlorinating agent, is performed in a reaction mixture which comprises less than 0.5% solvent by volume.

9. The process according to claim 8, wherein said reacting 2-(4-chlorophenyl)ethanol or a salt thereof, with said first chlorinating agent, is performed in a reaction mixture which comprises less than 0.1% solvent by volume.

10. The process according to claim 1, wherein said reacting 2-(4-chlorophenyl)ethanol or a salt thereof, with said first chlorinating agent, is performed at a temperature of about 50° C. to about 75° C.

11. The process according to claim 1, wherein the molar ratio of said first chlorinating agent and said 2-(4-chlorophenyl)ethanol or a salt thereof is about 1.2:1 to about 1:1.

12. The process according to claim 1, wherein the molar ratio of said 2-(4-chlorophenyl)ethanol or a salt thereof and said first catalyst is about 20:1.

13. The process according to claim 1, wherein said reacting 1-chloro-4-(2-chloroethyl)benzene with 1-aminopropan-2-ol or a salt thereof, is performed in a reaction mixture which comprises less than 5% solvent by volume.

14. The process according to claim 13, wherein the molar ratio of said 1-aminopropan-2-ol or a salt thereof and said 1-chloro-4-(2-chloroethyl)benzene is about 5:1.

15. The process according to claim 13, wherein said reacting 1-chloro-4-(2-chloroethyl)benzene with 1-aminopropan-2-ol or a salt thereof, is performed in a reaction mixture which comprises less than 4% solvent by volume.

16. The process according to claim 15, wherein said reacting 1-chloro-4-(2-chloroethyl)benzene with 1-aminopropan-2-ol or a salt thereof, is performed in a reaction mixture which comprises less than 3% solvent by volume.

17. The process according to claim 16, wherein said reacting 1-chloro-4-(2-chloroethyl)benzene with 1-aminopropan-2-ol or a salt thereof, is performed in a reaction mixture which comprises less than 2% solvent by volume.

18. The process according to claim 17, wherein said reacting 1-chloro-4-(2-chloroethyl)benzene with 1-aminopropan-2-ol or a salt thereof, is performed in a reaction mixture which comprises less than 1% solvent by volume.

19. The process according to claim 18, wherein said reacting 1-chloro-4-(2-chloroethyl)benzene with 1-aminopropan-2-ol or a salt thereof, is performed in a reaction mixture which comprises less than 0.5% solvent by volume.

20. The process according to claim 19, wherein said reacting 1-chloro-4-(2-chloroethyl)benzene with 1-aminopropan-2-ol or a salt thereof, is performed in a reaction mixture which comprises less than 0.1% solvent by volume.

21. The process according to claim 1, wherein said reacting 1-chloro-4-(2-chloroethyl)benzene with 1-aminopropan-2-ol or a salt thereof, is performed in the presence of toluene.

22. The process according to claim 13, wherein said reacting 1-chloro-4-(2-chloroethyl)benzene with 1-aminopropan-2-ol or a salt thereof, is performed at a temperature of about 75° C. to about 100° C.

23. The process according to claim 1, wherein said second chlorinating agent comprises thionyl chloride.

24. The process according to claim 23, wherein said reacting said 1-(4-chlorophenethylamino)propan-2-ol or a salt thereof, with said second chlorinating agent, comprises formation of a reaction mixture by addition of said 1-(4-chlorophenethylamino)propan-2-ol or a salt thereof to said second chlorinating agent.

25. The process according to claim 23, wherein said reacting said 1-(4-chlorophenethylamino)propan-2-ol or a salt thereof, with said second chlorinating agent, comprises formation of a reaction mixture by addition of said second chlorinating agent to said 1-(4-chlorophenethylamino)propan-2-ol or a salt thereof.

26. The process according to claim 25, wherein said addition takes about 1 hour or less.

27. The process according to claim 25, wherein said addition is performed at a rate such that said reaction mixture is substantially free of solid precipitates during said addition.

28. The process according to claim 1, wherein said reacting 1-(4-chlorophenethylamino)propan-2-ol or a salt thereof, with said second chlorinating agent, is performed in the presence of a second aprotic solvent, wherein said second aprotic solvent comprises toluene.

29. The process according to claim 1, wherein said reacting 1-(4-chlorophenethylamino)propan-2-ol or a salt thereof, with said second chlorinating agent, is performed at a temperature of about 50° C. to about 75° C.

30. The process according to claim 1, wherein the molar ratio of said second chlorinating agent and said 1-(4-chlorophenethylamino)propan-2-ol or a salt thereof is about 2:1 to about 1:1.

31. The process according to claim 1, wherein said reacting 1-(4-chlorophenethylamino)propan-2-ol or a salt thereof, with a second chlorinating agent, is performed with less than 1 mol % of an amide catalyst.

32. The process of claim 1, further comprising preparing (R)-8-chloro-1-methyl-2,3,4,5-tetrahydro-1H-3-benzazepine or a salt thereof from said compound selected from: 2-chloro-N-(4-chlorophenethyl)propan-1-amine (Compound VI) and salts thereof.

33. The process of claim 32, further comprising formulating said (R)-8-chloro-1-methyl-2,3,4,5-tetrahydro-1H-3-benzazepine or a salt thereof as a pharmaceutical composition.

34. The process according to claim 1, wherein said reacting 1-(4-chlorophenethylamino)propan-2-ol or a salt thereof, with a second chlorinating agent, is performed with less than 0.5 mol % of an amide catalyst.

35. The process according to claim 34, wherein said reacting 1-(4-chlorophenethylamino)propan-2-ol or a salt thereof, with a second chlorinating agent, is performed with less than 0.1 mol % of an amide catalyst.

36. The process according to claim 35, wherein said reacting 1-(4-chlorophenethylamino)propan-2-ol or a salt thereof, with a second chlorinating agent, is performed with less than 0.01 mol % of an amide catalyst.

37. The process according to claim 36, wherein said reacting 1-(4-chlorophenethylamino)propan-2-ol or a salt thereof, with a second chlorinating agent, is performed with less than 0.001 mol % of an amide catalyst.

38. The process of claim 1, further comprising reacting said compound selected from: 2-chloro-N-(4-chlorophenethyl)propan-1-amine (Compound VI) and salts thereof with a cyclizing reagent for a time and under conditions suitable for forming a mixture of (R)-8-chloro-1-methyl-2,3,4,5-tetrahydro-1H-3-benzazepine and (S)-8-chloro-1-methyl-2,3,4,5-tetrahydro-1H-3-benzazepine, or salts thereof.

39. The process of claim 38, wherein said cyclizing reagent is $AlCl_3$.

40. The process of claim 38, further comprising resolving a mixture of (R)-8-chloro-1-methyl-2,3,4,5-tetrahydro-1H-3-benzazepine and (S)-8-chloro-1-methyl-2,3,4,5-tetrahydro-1H-3-benzazepine or salts thereof, said method comprising the steps of: contacting said mixture with a chiral resolving acid to form chiral resolving acid salts of said (R)-8-chloro-1-methyl-2,3,4,5-tetrahydro-1H-3-benzazepine and (S)-8-chloro-1-methyl-2,3,4,5-tetrahydro-1H-3-benzazepine, wherein said chiral resolving acid comprises substantially one stereoisomer; and precipitating said chiral resolving acid salts, wherein the resulting precipitate is enriched in the chiral resolving acid salt of (R)-8-chloro-1-methyl-2,3,4,5-tetrahydro-1H-3-benzazepine.

41. The process of claim 40, further comprising reacting a chiral resolving acid salt of (R)-8-chloro-1-methyl-2,3,4,5-tetrahydro-1H-3-benzazepine with a pharmaceutically acceptable acid for a time and under conditions suitable for forming a pharmaceutically acceptable acid salt of (R)-8-chloro-1-methyl-2,3,4,5-tetrahydro-1H-3-benzazepine.

42. The process of claim 41, wherein said pharmaceutically acceptable acid is hydrochloric acid.

43. The process of claim 40, wherein said chiral resolving acid is L-(+)-tartaric acid.

44. A process for preparing a compound selected from: 2-chloro-N-(4-chlorophenethyl)propan-1-amine (Compound VI), which has the following structure:

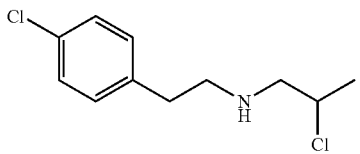

VI and salts thereof; comprising the following steps:
(a) reacting 2-(4-chlorophenyl)ethanol (Compound II):

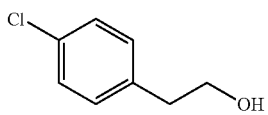

II or a salt thereof, with a first chlorinating agent to form 1-chloro-4-(2-chloroethyl)benzene (Compound III):

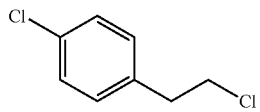

III wherein
said first chlorinating agent comprises thionyl chloride,
said reacting 2-(4-chlorophenyl)ethanol or a salt thereof, with said first chlorinating agent, is performed in a reaction mixture which comprises less than 5% solvent by volume,
said reacting 2-(4-chlorophenyl)ethanol or a salt thereof, with said first chlorinating agent, is performed at a temperature of about 50° C. to about 75° C.,
the molar ratio of said first chlorinating agent and said 2-(4-chlorophenyl)ethanol or a salt thereof is about 1.2:1 to about 1:1,
said reacting 2-(4-chlorophenyl)ethanol or a salt thereof, with said first chlorinating agent, is performed in the presence of a first catalyst, wherein said first catalyst comprises N,N-dimethylformamide, and
the molar ratio of said 2-(4-chlorophenyl)ethanol or a salt thereof and said first catalyst is about 25:1 to about 5:1;

(b) reacting said 1-chloro-4-(2-chloroethyl)benzene (Compound III) with 1-aminopropan-2-ol (Compound IV):

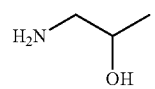

IV or a salt thereof, to form 1-(4-chlorophenethylamino)propan-2-ol (Compound V):

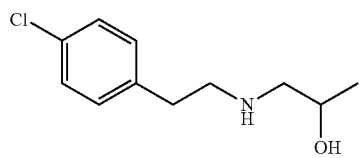

V or a salt thereof
wherein
said reacting 1-chloro-4-(2-chloroethyl)benzene with 1-aminopropan-2-ol or a salt thereof, is performed in a reaction mixture which comprises less than 5% solvent by volume,
said reacting 1-chloro-4-(2-chloroethyl)benzene with 1-aminopropan-2-ol or a salt thereof, is performed at a temperature of about 75° C. to about 100° C., and
the molar ratio of said 1-aminopropan-2-ol or a salt thereof and said 1-chloro-4-(2-chloroethyl)benzene is about 5:1; and
(c) reacting said 1-(4-chlorophenethylamino)propan-2-ol (Compound V) or a salt thereof, with a second chlorinating agent to form said compound selected from: 2-chloro-N-(4-chlorophenethyl)propan-1-amine (Compound VI) and salts thereof wherein
said second chlorinating agent comprises thionyl chloride,
said reacting 1-(4-chlorophenethylamino)propan-2-ol or a salt thereof, with said second chlorinating agent, is performed at a temperature of about 50° C. to about 75° C.,
the molar ratio of said second chlorinating agent and said 1-(4-chlorophenethylamino)propan-2-ol or a salt thereof is about 2:1 to about 1:1, and
said reacting 1-(4-chlorophenethylamino)propan-2-ol or a salt thereof, with a second chlorinating agent, is performed with less than 1 mol % of an amide catalyst.

* * * * *